United States Patent
Itkowitz et al.

(10) Patent No.: US 12,383,360 B2
(45) Date of Patent: *Aug. 12, 2025

(54) RATCHETING FOR MASTER ALIGNMENT OF A TELEOPERATED MINIMALLY INVASIVE SURGICAL INSTRUMENT

(71) Applicant: INTUITIVE SURGICAL OPERATIONS, INC., Sunnyvale, CA (US)

(72) Inventors: Brandon D. Itkowitz, San Jose, CA (US); Simon P. DiMaio, San Carlos, CA (US); William C. Nowlin, Los Altos Hills, CA (US); Gunter D. Niemeyer, Pasadena, CA (US); David S. Mintz, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/655,041

(22) Filed: May 3, 2024

(65) Prior Publication Data

US 2024/0285362 A1 Aug. 29, 2024

Related U.S. Application Data

(63) Continuation of application No. 18/309,110, filed on Apr. 28, 2023, now Pat. No. 12,011,244, which is a
(Continued)

(51) Int. Cl.
*B25J 9/16* (2006.01)
*A61B 34/00* (2016.01)
(Continued)

(52) U.S. Cl.
CPC .............. *A61B 34/37* (2016.02); *A61B 34/25* (2016.02); *A61B 34/30* (2016.02); *A61B 34/35* (2016.02);
(Continued)

(58) Field of Classification Search
USPC ........... 606/1, 130; 318/568.11–568.22, 572; 700/245–264
See application file for complete search history.

(56) References Cited

U.S. PATENT DOCUMENTS 6,364,888 B1 * 4/2002 Niemeyer .............. A61B 34/37
348/E13.016
6,424,885 B1 7/2002 Niemeyer et al.
(Continued)

FOREIGN PATENT DOCUMENTS

CN 1533745 A 10/2004
WO WO-2007120353 A2 10/2007
(Continued)

OTHER PUBLICATIONS

Cunningham, Steve, "3D Viewing and Rotation Using Orthonormal Bases," Graphic Gems, Andrew S. Glassner, ed., 1990, pp. 516-521, Academic Press, Inc., Boston, MA, USA.
(Continued)

*Primary Examiner* — Jonathan L Sample
(74) *Attorney, Agent, or Firm* — Artegis Law Group, LLP

(57) ABSTRACT

Techniques for ratcheting an alignment between an input means and an instrument include a teleoperated system comprising a robotic means configured to support an instrument, an input means configured to be manipulated by an operator to command motion of the instrument, and a ratcheting means. The ratcheting means is configured to determine first rotation values describing an orientation of the input means; determine second rotation values describ-
(Continued)

ing an orientation of the instrument; determine, based on the first rotation values and the second rotation values, an orientation error between the orientation of the input means and the orientation of the instrument; generate, based on the orientation error, a motion command for the instrument to reduce the orientation error by increasing an alignment between the input means and the instrument; and command the robotic means to move in accordance with the motion command.

20 Claims, 10 Drawing Sheets

Related U.S. Application Data continuation of application No. 17/107,862, filed on Nov. 30, 2020, now Pat. No. 11,672,619, which is a continuation of application No. 16/862,412, filed on Apr. 29, 2020, now Pat. No. 10,881,473, which is a continuation of application No. 16/353,932, filed on Mar. 14, 2019, now Pat. No. 10,675,109, which is a continuation of application No. 15/706,883, filed on Sep. 18, 2017, now Pat. No. 10,278,783, which is a continuation of application No. 15/399,600, filed on Jan. 5, 2017, now Pat. No. 9,814,537, which is a continuation of application No. 14/996,073, filed on Jan. 14, 2016, now Pat. No. 9,579,164, which is a continuation of application No. 14/534,526, filed on Nov. 6, 2014, now Pat. No. 9,265,584, which is a continuation of application No. 13/839,438, filed on Mar. 15, 2013, now Pat. No. 8,903,549, which is a continuation of application No. 12/495,213, filed on Jun. 30, 2009, now Pat. No. 8,423,186.

(51) Int. Cl.
  *A61B 34/30* (2016.01)
  *A61B 34/35* (2016.01)
  *A61B 34/37* (2016.01)
  *A61B 90/10* (2016.01)
  *B25J 3/00* (2006.01)
  *A61B 17/00* (2006.01)

(52) U.S. Cl.
  CPC ............ *A61B 90/10* (2016.02); *B25J 3/00* (2013.01); *B25J 9/1669* (2013.01); *B25J 9/1689* (2013.01); *A61B 2017/00725* (2013.01); *A61B 2034/305* (2016.02); *G05B 2219/45117* (2013.01); *Y10S 901/27* (2013.01); *Y10S 901/41* (2013.01)

(56) References Cited

U.S. PATENT DOCUMENTS

| | | | |
|---|---|---|---|
| 6,594,552 B1 | 7/2003 | Nowlin et al. | |
| 6,630,993 B1 | 10/2003 | Hedges et al. | |
| 6,766,204 B2 | 7/2004 | Niemeyer et al. | |
| 6,786,896 B1 | 9/2004 | Madhani et al. | |
| 6,853,879 B2 | 2/2005 | Sunaoshi | |
| 7,126,303 B2 | 10/2006 | Farritor et al. | |
| 7,339,341 B2 | 3/2008 | Oleynikov et al. | |
| 7,492,116 B2 | 2/2009 | Oleynikov et al. | |
| 7,656,106 B2 * | 2/2010 | Iwashita | G05B 19/4141 318/68 |
| 8,423,186 B2 * | 4/2013 | Itkowitz | A61B 34/35 700/250 |
| 8,903,549 B2 | 12/2014 | Itkowitz et al. | |
| 8,924,021 B2 | 12/2014 | Dariush et al. | |
| 9,265,584 B2 | 2/2016 | Itkowitz et al. | |
| 9,579,164 B2 | 2/2017 | Itkowitz et al. | |
| 9,795,453 B2 * | 10/2017 | Tierney | A61B 34/35 |
| 9,814,537 B2 | 11/2017 | Itkowitz et al. | |
| 10,278,783 B2 | 5/2019 | Itkowitz et al. | |
| 10,675,109 B2 | 6/2020 | Itkowitz et al. | |
| 10,881,473 B2 | 1/2021 | Itkowitz et al. | |
| 11,672,619 B2 | 6/2023 | Itkowitz et al. | |
| 12,011,244 B2 | 6/2024 | Itkowitz et al. | |
| 2002/0128552 A1 * | 9/2002 | Nowlin | A61B 34/35 600/427 |
| 2002/0133173 A1 * | 9/2002 | Brock | A61B 34/20 606/130 |
| 2003/0120283 A1 | 6/2003 | Stoianovici et al. | |
| 2004/0111183 A1 | 6/2004 | Sutherland et al. | |
| 2004/0254680 A1 | 12/2004 | Sunaoshi | |
| 2005/0024331 A1 | 2/2005 | Berkley et al. | |
| 2005/0166413 A1 | 8/2005 | Crampton et al. | |
| 2005/0222554 A1 * | 10/2005 | Wallace | A61B 8/12 606/1 |
| 2005/0251110 A1 | 11/2005 | Nixon | |
| 2006/0030840 A1 * | 2/2006 | Nowlin | A61B 34/70 606/1 |
| 2006/0178556 A1 | 8/2006 | Hasser et al. | |
| 2006/0241414 A1 * | 10/2006 | Nowlin | A61B 34/35 600/431 |
| 2007/0013336 A1 * | 1/2007 | Nowlin | A61B 34/30 318/568.21 |
| 2007/0055291 A1 | 3/2007 | Birkmeyer et al. | |
| 2007/0080658 A1 | 4/2007 | Farritor et al. | |
| 2007/0197896 A1 | 8/2007 | Moll et al. | |
| 2007/0299427 A1 * | 12/2007 | Yeung | A61B 34/77 606/1 |
| 2008/0009697 A1 | 1/2008 | Haider et al. | |
| 2008/0046122 A1 | 2/2008 | Manzo et al. | |
| 2008/0111513 A1 | 5/2008 | Farritor et al. | |
| 2008/0114494 A1 * | 5/2008 | Nixon | A61B 34/30 700/254 |
| 2008/0132913 A1 | 6/2008 | Brock et al. | |
| 2008/0154246 A1 | 6/2008 | Nowlin et al. | |
| 2008/0235970 A1 | 10/2008 | Crampton | |
| 2008/0319557 A1 | 12/2008 | Summers et al. | |
| 2009/0000136 A1 | 1/2009 | Crampton | |
| 2009/0088634 A1 * | 4/2009 | Zhao | A61B 1/00193 600/425 |
| 2009/0088773 A1 | 4/2009 | Zhao et al. | |
| 2009/0088774 A1 | 4/2009 | Swarup et al. | |
| 2009/0088897 A1 | 4/2009 | Zhao et al. | |
| 2009/0163929 A1 | 6/2009 | Yeung et al. | |
| 2009/0192524 A1 * | 7/2009 | Itkowitz | B25J 9/1689 606/130 |
| 2009/0259340 A1 | 10/2009 | Umemoto et al. | |
| 2009/0326552 A1 * | 12/2009 | Diolaiti | A61B 90/10 606/130 |
| 2010/0225209 A1 * | 9/2010 | Goldberg | G16H 20/40 312/209 |
| 2010/0300230 A1 | 12/2010 | Helmer | |
| 2010/0332031 A1 * | 12/2010 | Itkowitz | A61B 34/30 700/245 |
| 2011/0118748 A1 | 5/2011 | Itkowitz | |
| 2011/0257653 A1 | 10/2011 | Hughes et al. | |
| 2011/0275957 A1 | 11/2011 | Bhandari | |
| 2011/0304819 A1 | 12/2011 | Juhasz et al. | |
| 2011/0306986 A1 | 12/2011 | Lee et al. | |
| 2011/0319714 A1 | 12/2011 | Roelle et al. | |
| 2011/0319910 A1 | 12/2011 | Roelle et al. | |
| 2013/0010081 A1 | 1/2013 | Tenney et al. | |
| 2013/0238127 A1 | 9/2013 | Ohta et al. | |
| 2014/0163664 A1 | 6/2014 | Goldsmith | |
| 2016/0210882 A1 | 7/2016 | Gulasy et al. | |
| 2016/0256223 A1 | 9/2016 | Haimerl et al. | |

(56) References Cited

U.S. PATENT DOCUMENTS

2017/0095301 A1    4/2017  Brisson
2023/0329817 A1   10/2023  Itkowitz et al.

FOREIGN PATENT DOCUMENTS

WO    WO-2008133956 A2   11/2008
WO    WO-2009023801 A1    2/2009

OTHER PUBLICATIONS

Extended European Search Report for Application No. 16160639.7, mailed on Aug. 12, 2016, 8 pages.

Extended European Search Report for Application No. 18203548.5 mailed on May 27, 2019, 12 pages.

Hekstra, Gerben J. and Ed F.A. Deprettere, "Fast Rotations: Low-cost Arithmetic Methods for Orthonormal Rotation," Proceedings of the 13th IEEE Symposium on Computer Arithmetic, Jul. 1997, pp. 116-125, IEEE.

PCT/US10/38256 International Search Report and Written Opinion of the international Searching Authority, mailed Aug. 20, 2010, 15 pages.

Stroz, Kazimierz, "Derivation of the Rotation Matrix in General Rectilinear Systems by Means of Vector and Matrix Formalism," Journal of Applied Crystallography, Dec. 1996, pp. 736-737, vol. 29, Part 6, International Union of Crystallography, GB.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

RATCHETING FOR MASTER ALIGNMENT OF A TELEOPERATED MINIMALLY INVASIVE SURGICAL INSTRUMENT

RELATED APPLICATIONS

This application is a continuation of U.S. patent application Ser. No. 18/309,110 (filed Apr. 28, 2023), which is a continuation of U.S. patent application Ser. No. 17/107,862 (filed Nov. 30, 2020) and now U.S. Pat. No. 11,672,619, which is a continuation of U.S. patent application Ser. No. 16/862,412 (filed Apr. 29, 2020) and now U.S. Pat. No. 10,881,473, which is a continuation of U.S. patent application Ser. No. 16/353,932 (filed Mar. 14, 2019) and now U.S. Pat. No. 10,675,109, which is a continuation of U.S. patent application Ser. No. 15/706,883 (filed Sep. 18, 2017 and now U.S. Pat. No. 10,278,783), which is a continuation of U.S. patent application Ser. No. 15/399,600 (filed Jan. 5, 2017 and now U.S. Pat. No. 9,814,537), which is a continuation of U.S. patent application Ser. No. 14/996,073 (filed Jan. 14, 2016 and now U.S. Pat. No. 9,579,164), which is a continuation of U.S. patent application Ser. No. 14/534,526 (filed Nov. 6, 2014 and now U.S. Pat. No. 9,265,584), which is a continuation of U.S. patent application Ser. No. 13/839,438 (filed Mar. 15, 2013 and now U.S. Pat. No. 8,903,549), which is a continuation of U.S. patent application Ser. No. 12/495,213 (filed Jun. 30, 2009 and now U.S. Pat. No. 8,423,186). The full disclosures of these related applications are incorporated by reference herein for all purposes.

BACKGROUND

1. Field of Invention

Aspects of this invention are related to teleoperated minimally invasive surgical systems, and more particularly are related to controlling orientation of master and slave surgical instrument tips in a teleoperated minimally invasive surgical system.

2. Related Art

The da Vinci® surgical system, manufactured by Intuitive Surgical, Inc., Sunnyvale, California, is a minimally invasive, teleoperated robotic system that offers patients many benefits, such as reduced trauma to the body, faster recovery and shorter hospital stay. One component of the da Vinci® Surgical System is a master tool manipulator that a surgeon uses to manipulate a surgical instrument, referred to as a slave surgical instrument.

The master grip of the master tool manipulator is specially designed to be both ergonomic and intuitive for controlling the slave surgical instrument. The surgeon holds the master grip in a particular way using his/her forefinger and thumb, so that targeting and grasping involves intuitive pointing and pinching motions.

To enable intuitive control of the slave surgical instrument, the master grip must be aligned in orientation with the slave surgical instrument tip in the view reference frame of the stereoscopic viewer. The motions of the slave surgical instrument tip follow master motions via teleoperation and are consistent in both directions of motion as well as absolute orientation. If orientation alignment is not achieved, the slave surgical instrument tip may still rotate in the desired direction, but the slave surgical instrument tip neither points in the same absolute direction nor rolls along the same axis as the surgeon is pointing.

The master tool manipulator uses motors in a gimbal assembly to actively align the orientation axes of the master grip with the associated slave surgical instrument tip in view coordinates. This alignment happens automatically before the surgeon engages teleoperation. Moreover, the system automatically preserves this alignment during manipulation of the camera or instrument outer axes.

Specifically, when entering following on the da Vinci® surgical system, the master grip must be aligned with the orientation of the slave surgical instrument tip before the da Vinci® surgical system operates properly in following. The present system performs a master alignment whenever the system transitions from a mode where this orientation alignment may have been compromised (after a tool change, camera clutch, slave clutch, swapping of arms in a 4th arm system etc.).

A master alignment calculates a set of master wrist joint angles that cause the orientation of the master grip to match the orientation of the slave surgical instrument tip, without changing the master grip position. The master wrist joints are then commanded to match the calculated angles using the motors.

The da Vinci® surgical system checks that the master and slave orientations match before allowing the user to enter following. If the orientations don't match (presumably because the user has over powered the master and not allowed the master to complete the alignment) a warning message is displayed and the master alignment is attempted again. This often slows down the surgeon's entry into following and requires a powered master tool manipulator with motors in the gimbal assembly to move master wrist joints into the proper orientation.

SUMMARY OF THE INVENTION

A minimally invasive surgical system includes a slave surgical instrument having a slave surgical instrument tip and a master grip. The master grip is coupled to the slave surgical instrument tip by a teleoperation servo control system. In one aspect, a ratcheting system, within the teleoperation servo control system, seamlessly and continuously improves the alignment, in a common coordinate frame of reference, of the master grip with respect to the slave surgical instrument tip as the master grip is moved.

The ratcheting system results in intuitive alignment between the master grip and the slave surgical instrument tip. Also, the ratcheting system provides a direct association between what the surgeon is doing, manipulating the master grip, and what the surgeon is seeing at a surgeon's console, movement of the slave surgical instrument tip in the display. This is achieved without the delays associated with the conventional powered alignments before following could be entered. Also, the ratcheting system, in one aspect, eliminates the need for the powered master grip and permits use of lower cost readily available components as the master grip.

In one aspect, the slave surgical instrument tip and the master grip have Cartesian position components and orientation components in a common coordinate reference frame. The ratcheting system can achieve alignment for all components, a subset of components, e.g., the orientation components or the Cartesian components, or in a component-wise fashion for a particular set of components.

A ratcheting system, in the teleoperation servo control system, is (i) coupled to the master grip to receive the alignment of the master grip in a common coordinate frame, and (ii) coupled to the slave surgical instrument. The ratcheting system controls the motion of the slave by continuously reducing the alignment error in the common coordinate frame, as the master grip moves. This is done without autonomous motion of the slave surgical instrument tip and without autonomous motion of the master grip.

In one aspect, the alignment error in the common coordinate frame is an orientation error. The orientation error comprises an angle. In one aspect, the angle is an angle $\theta_e$ defined as:

$$\theta_e = \cos^{-1}[0.5*(R_{\Delta 11} + R_{\Delta 22} + R_{\Delta 33} - 1)],$$

where $R_{\Delta 11}$, $R_{\Delta 22}$, $R_{\Delta 33}$ are diagonal elements of a relative rotation matrix $R_\Delta$. In another aspect, the angle is one Euler angle in a set of Euler angles.

In another aspect, the ratcheting system includes an introduce control loop error controller that introduces a control system error in the alignments of the slave surgical instrument tip and the master grip in the common frame of reference. For example, an angular velocity of the slave surgical instrument is penalized based upon an amount of misalignment in the common reference frame between the slave surgical instrument tip and the master grip. In still another aspect, the ratcheting system includes a roll-joint limit controller for determining whether motion of the slave surgical instrument has reached a joint limit and constraining motion of the slave surgical instrument tip upon reaching the joint limit. In still yet another aspect, the ratcheting system includes multiple orientation solutions, a best orientation controller selects one solution from the multiple orientation solutions that is closest to the orientation of the master grip.

A method using the above minimally surgical system includes controlling motion of a slave surgical instrument tip in the minimally invasive surgical system with motion of a master grip in the minimally invasive surgical system. In this method, a ratcheting system in the minimally invasive surgical system receives an alignment of the slave surgical instrument tip and an alignment of the master grip, both in a common frame of reference. The ratcheting system ratchets the alignment of the slave surgical instrument tip to the alignment of the master grip by continuously reducing an alignment error between the alignments, as the master grip moves, without autonomous motion of the slave surgical instrument tip and without autonomous motion of the master grip.

In one aspect, the ratcheting includes moving the slave surgical instrument tip and the master grip in a same relative way upon engagement of following by the minimally invasive surgical system irrespective of the alignments in the common reference frame. The ratcheting also includes bleeding off the alignment error in the common frame of reference by using a new alignment error when the motion of the master grip reduces the alignment error in the common reference frame, and by using a current alignment error in the common reference frame when the motion of the master grip does not reduces the alignment error thereby continuously reducing the alignment error between the alignments in the common reference frame.

The ratcheting system also generates a new alignment for the slave surgical instrument using the new alignment error, and sends a command to the slave surgical instrument based on the new alignment.

In another aspect, the ratcheting system introduces a control error between the slave surgical instrument alignment and the master grip alignment. The introduction of a control error further includes penalizing a commanded angular velocity for the slave surgical instrument tip based on the current alignment error.

Figure 1:
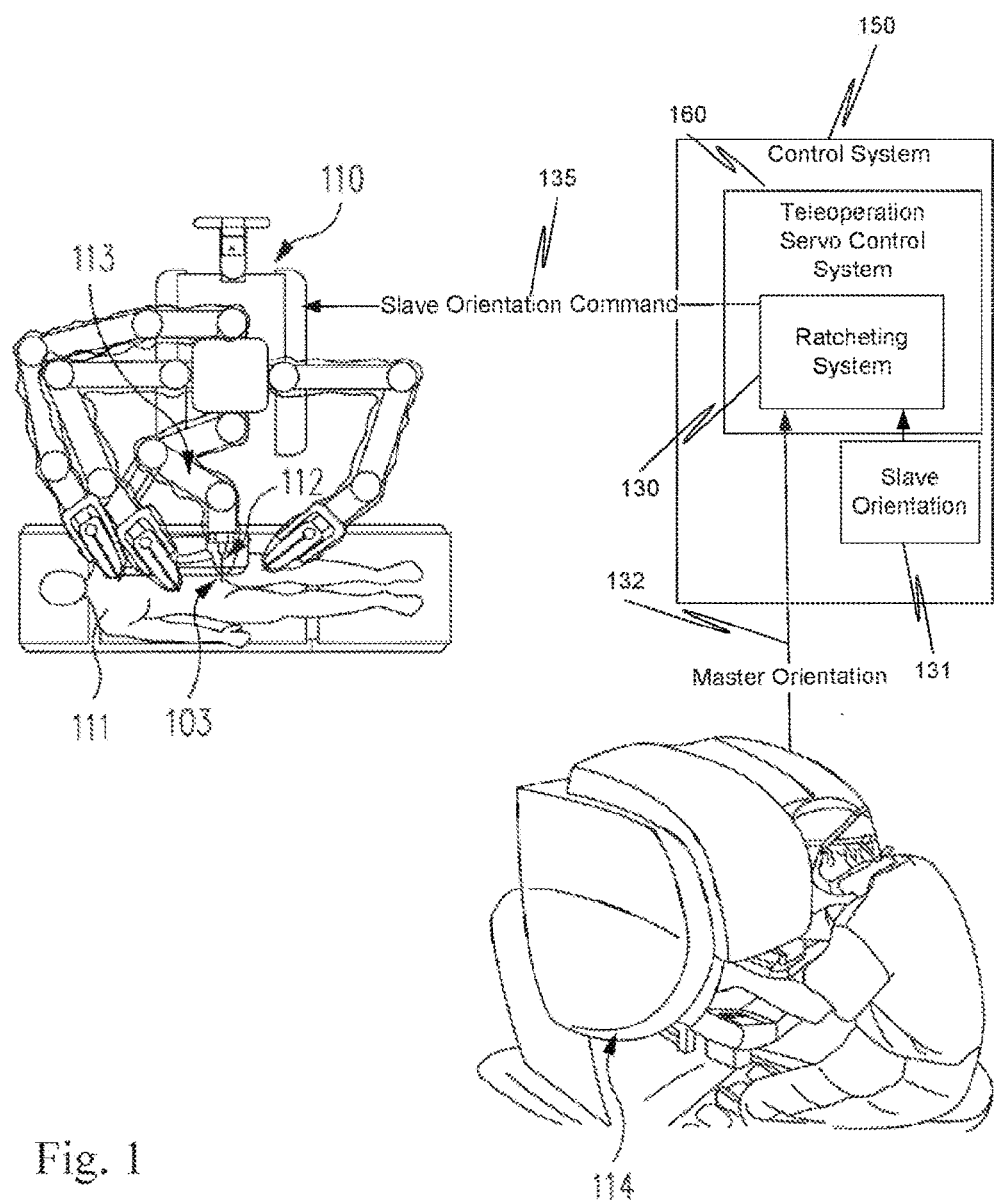
FIG. 1 is a diagrammatic view of a minimally invasive surgical robot which includes a teleoperation servo control system with a ratcheting system.

In the drawings, the first digit of a figure number indicates the figure in which the element with that figure number first appeared.

DETAILED DESCRIPTION

Aspects of this invention replace the powered master tool manipulator, such as that used in the da Vinci® Surgical Robot System manufactured by Intuitive Surgical, Inc. of Sunnyvale, California with an unpowered master tool manipulator that includes at least one master grip. In minimally invasive surgical system 100, a surgeon, at a console 114, grasps a master grip (not shown) between the thumb and forefinger so that targeting and grasping still involves intuitive pointing and pinching motions. The motion of the master grip is used by control system 150, as described more completely below, to move an end-effector of slave surgical instrument 112.

Unlike the conventional system that required the surgeon to wait until the alignment of the master grip and the slave surgical instrument end-effector, in a common frame of reference, were positioned so that following could be entered, a ratcheting system 130, within a teleoperation servo control system 160 of control system 150, is activated when the surgeon starts to move the master grip. Irrespective of the alignment between the master grip and the end-effector of slave surgical instrument 112 in the common frame of reference, teleoperation servo control system 160 enters following between the master grip and the surgical instrument end-effector, sometimes called a slave surgical instrument tip, and activates ratcheting system 130.

Ratcheting system 130 seamlessly and continuously improves the alignment of the master grip with respect to the slave surgical instrument tip, in the common frame of reference, as the master grip is moved. Ratcheting system 130 ratchets the movement of the slave surgical instrument tip to continuously and seamlessly reduce any alignment error, in the common frame of reference, between the slave surgical instrument tip and the master grip. Ratcheting system 130 achieves the alignment without autonomous motion of either the master grip, or the slave surgical instrument tip.

Ratcheting system 130 results in intuitive alignment between the master grip and the slave surgical instrument tip as viewed by the surgeon. Also, ratcheting system 130 provides a direct association between what the surgeon is doing, manipulating the master grip, and what the surgeon is seeing at console 114, movement of the slave surgical instrument tip in the display. This is achieved without the delays associated with the conventional powered alignments before following could be entered. Also, ratcheting system 130 eliminates the need for the powered master grip and permits use of lower cost readily available components as the master grip.

Console 114 (FIGS. 1 and 2A) includes a master display, which displays at least a stereoscopic image 210 (FIG. 2A) of a surgical site 103 of patient 111. Stereoscopic image 210 typically includes an image 203 of surgical site 103, an image 212 of a part of surgical instrument 112, and an image of a tip 212T of slave surgical instrument 112. Console 114 also includes one or more foot pedals (Not shown).

Console 114 (FIG. 1) is connected to a control system 150 that is turn is connected to a cart 110, which supports a plurality of robotic arms that includes robotic arm 113. Slave surgical instrument 112 is held and positioned by robotic arm 113. While it is not shown in FIG. 1, an endoscope, held by another of the robotic arms, is typically used to provide image 210.

Figure 2A:
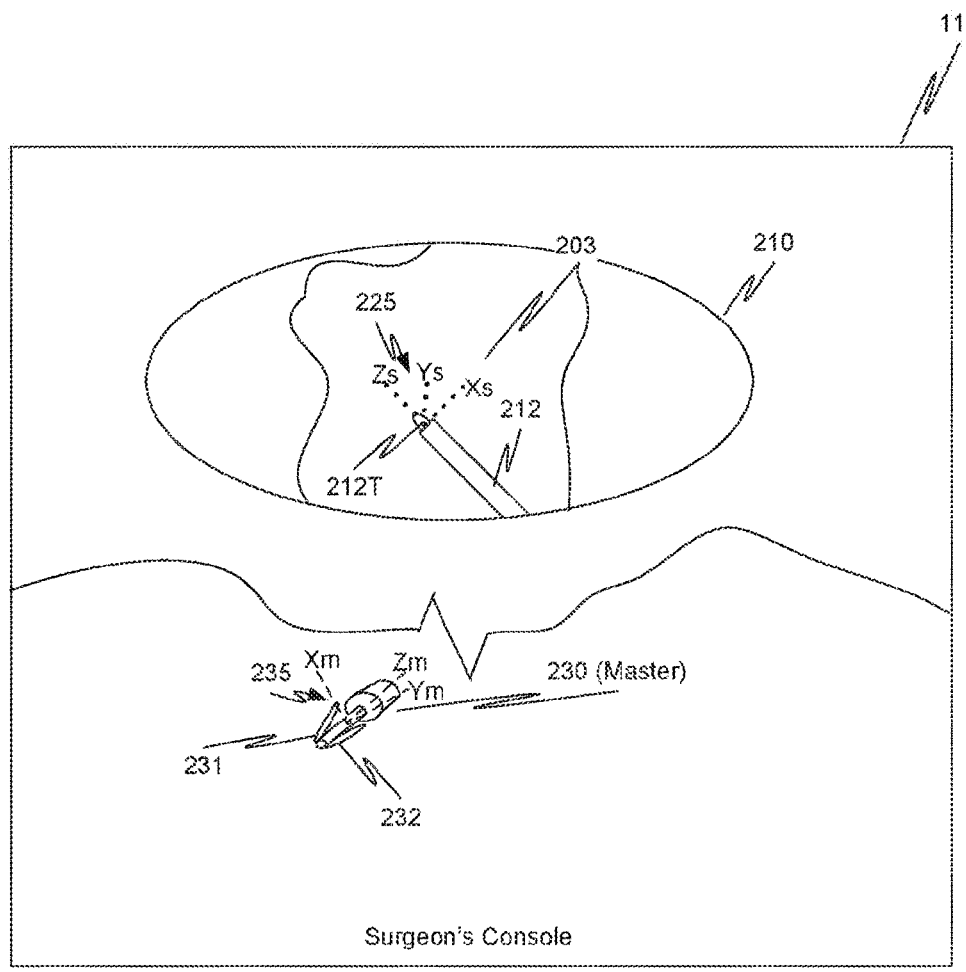
FIG. 2A is diagrammatic view of parts of the surgeon's console of FIG. 1 for a minimally invasive surgical robot of FIG. 1.

The surgeon sits comfortably and looks into the master display on console 114 throughout surgery. The surgeon performs a medical procedure by manipulating at least master grip 230 (FIG. 2A). In response to master alignment information 132 from master grip 230, teleoperation servo control system 160 in control system 150 (FIG. 1) causes corresponding robotic arm 113 to position slave surgical instrument 112 using a slave command 135. Typically, console 114 includes at least two master grips and each master grip controls a different robotic arm and attached surgical instrument. Herein a single master grip 230 is considered. In view of this description, ratcheting system 130 can be implemented for any desired number of master grips.

The master display is positioned on console 114 (FIG. 1) near the surgeon's hands so that image 210 (FIG. 2A), which is seen in the master display, is oriented so that the surgeon feels that she or he is actually looking directly down onto surgical site 103. Image 212 of tool 112 appears to be located substantially where the surgeon's hands are located and oriented substantially as the surgeon would expect tool 112 to be based on the position of her/his hand. However, the surgeon cannot see the position or orientation of master grip 230 while viewing image 210.

The real-time image from the endoscope is projected into perspective image 210 such that the surgeon can manipulate a surgical instrument end-effector of tool 112, through its associated master grip 230, as if viewing the workspace in substantially true presence. By true presence, it is meant that the presentation of an image is a true perspective image simulating the viewpoint of an operator that is physically manipulating the surgical instrument. Thus, control system 150 transforms the coordinates of surgical instrument 112 to a perceived position so that the perspective image is the image that the surgeon would see if the endoscope were looking directly at surgical tool 112 from the surgeon's eye-level during an open cavity procedure.

Control system 150 performs various functions in system 100. Control system 150 receives the images from an endoscope and generates the stereoscopic image that the surgeon sees. In a conventional manner, control system 150 maps the slave alignment with respect to tip of the endoscope and maps the master alignment with respect to an aspect of the surgeon into the common frame of reference, sometimes called common reference frame, which is used by ratcheting system 130. See for example, U.S. Pat. No. 6,424,885, entitled "Camera Referenced Control in a Minimally invasive Surgical Apparatus," of Niemeyer et al. issued on Jul. 23, 2002, which is incorporated herein by reference in its entirety.

Control system 150 uses teleoperation servo control system 160 to translate and to transfer the mechanical motion of master grip 230 to an associated robotic arm 113 through control commands 135 so that the surgeon can effectively manipulate slave surgical instrument 112. The functions performed by teleoperation servo control system 160 are equivalent to the conventional functions when considered in conjunction with ratcheting system 130 that is also included in control system 150.

The number of surgical tools used at one time and consequently, the number of robotic arms being used in system 100 generally depends on the medical procedure to be performed and the space constraints within the operating room, among other factors. If it is necessary to change one or more of the tools being used during a procedure, an assistant may remove the tool no longer being used from its robot arm, and replace the tool with another tool from a tray in the operating room.

Although described as a control system 150, it is to be appreciated that control system 150 may be implemented in practice by any combination of hardware, software that is executed on a processor, and firmware. Also, its functions, as described herein, may be performed by one unit, or divided up among different components, each of which may be implemented in turn by any combination of hardware, software that is executed on a processor, and firmware. When divided up among different components, the components may be centralized in one location or distributed across system 100 for distributed processing purposes.

When there are only two master grips in system 100, and when the surgeon wants to control movement of a slave surgical instrument different from the two slave surgical instruments coupled to the two master grips, the surgeon may lock one or both of the two slave surgical instruments in place. The surgeon then associates one or both of the master grips with other slave surgical instruments held by other of the robotic arms and ratcheting system 130 becomes active with respect to those instruments.

Master grip 230 provides an alignment that is mapped into the common frame of reference, but is not powered, or at least does not include a powered wrist. However, the features of master grip 230, as described more completely below, can be used with a master grip that includes a powered wrist. As used herein, a powered wrist means a wrist that includes at least one motor to control the positioning of the wrist. The motor can be used to compensate for gravity and friction and to provide range of motion force-feedback, but any powered alignment capability is turned-off.

Master grip 230 includes two levers 231, 232, which the surgeon typically grasps between the thumb and forefinger. As the surgeon moves master grip 230, in one aspect, master grip alignment information 132 is provided to ratcheting system 130 in the common reference frame (See FIG. 2B for example). In this aspect, slave surgical instrument tip 212T has a slave alignment and ratcheting system 130 also receives this slave alignment mapped into the common reference frame. The two alignments used by ratcheting system 130 are in a common reference frame.

Figure 3A:
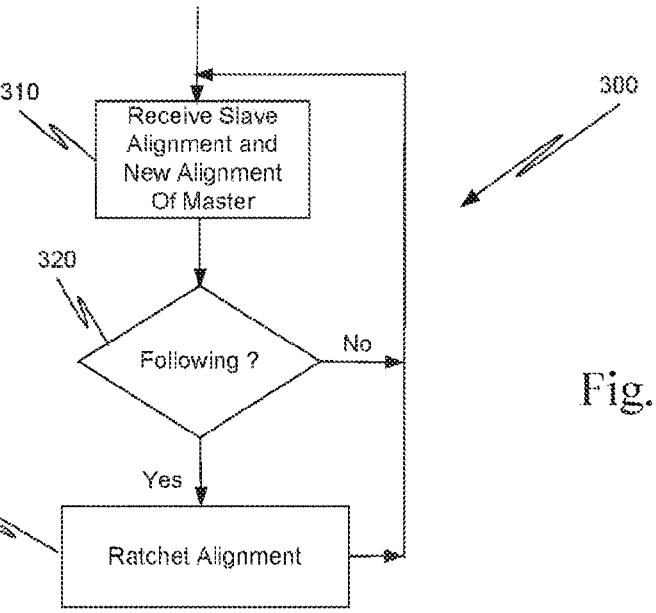
FIG. 3A is a process flow diagram for the ratcheting system.
Figure 3B:
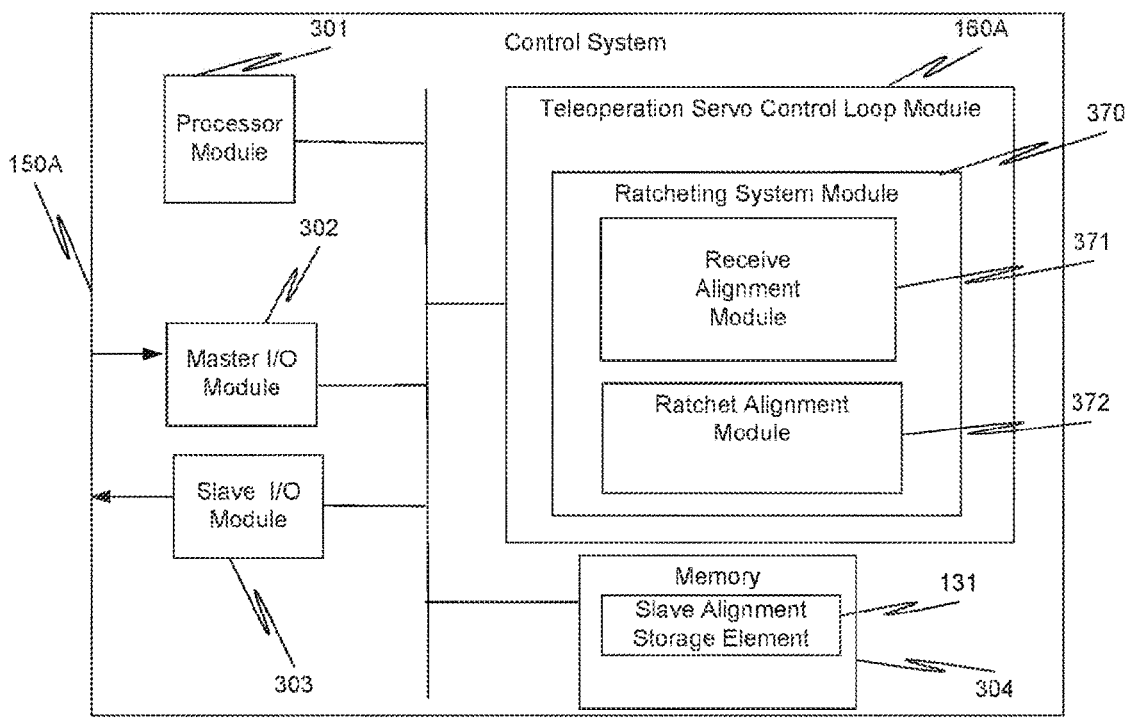
FIG. 3B is a block diagram of a control system including the modules used to implement the ratcheting system.

Thus, in one aspect of method 300 (FIG. 3A) is performed by ratcheting system 130. In this aspect, ratcheting system 130 includes a ratcheting system module 370 (FIG. 3B) that in turn includes a receive alignment module 371 and a ratchet alignment module 372.

A receive new alignment of master and slave operation 310, associated with receive orientation module 371, receives the master grip alignment and slave surgical instrument tip alignment in the common frame of reference. Ratcheting system 130 waits in following check operation 320 until following is initiated. Following check operation 320 should not be interpreted as requiring continuous polling, but rather simply interpreted as nothing is done with respect to the alignments in the common frame of reference until following is initiated.

Check operation 320 is used for illustration only and should not be viewed as limiting. The particular technique used to determine whether following is initiated could be based on an interrupt, an event, a particular flag or bit changing state, etc.

Upon engagement of following between master grip 230 and slave surgical instrument tip 212T, ratchet alignment process 330, which is associated with ratchet alignment module 372, generates commands that result in slave surgical instrument tip 212T moving in the same relative way as master grip 230 is moved irrespective of any alignment error in the common frame of reference between master grip 230 and slave surgical instrument tip 212T.

Note that for convenience, slave surgical instrument tip 212T is used in this description, as this is what the surgeon sees moving. The movement of this image corresponds directly to the movement of the slave surgical instrument tip itself. One knowledgeable in the field understands that movement of the image is a direct result of movement of the tip itself by the robot arm in response to a command from control system 150, as described herein.

As both master grip 230 and slave surgical instrument tip 212T move, ratchet alignment process 330 bleeds off any alignment error in the common reference frame between master grip 230 and slave surgical instrument tip 212T. For example, when the surgeon moves master grip 230 in a way that reduces the alignment error, ratchet alignment process 330 uses the reduced alignment error in the following between master grip 230 and slave surgical instrument tip 212T. Conversely, when the surgeon moves master grip 230 in a way that increases the alignment error, ratchet alignment process 330 uses the current alignment error, and not the increased alignment error, in the following between master grip 230 and slave surgical instrument tip 212T.

Thus, ratchet alignment process 330 seamlessly and continuously improves the absolute alignment of master grip 230 with respect to slave surgical instrument tip 212T. Ratchet alignment process 330 achieves the continuous improvement in absolute alignment without causing autonomous motion of either master grip 230 or slave surgical instrument tip 212T.

Ratcheting system 130 can ratchet an alignment error in the common reference frame that is either a position error or an orientation error. In the following examples, ratcheting of an orientation error in a common frame of reference is considered. However, the orientation error examples are illustrative only and are not intended to be limiting to the specific aspects described. In view of this disclosure, one knowledgeable in the field can apply the same principles to ratchet a position error.

In the following examples, as the surgeon moves master grip 230, in one aspect, a master grip orientation 235 in the common frame of reference is provided to ratcheting system 130. In this aspect, slave surgical instrument tip 212T has a slave orientation 225 in the common frame reference, which is equivalent to the orientation of the slave surgical instrument tip itself. Ratcheting system 130 also receives this slave orientation in the common frame of reference. In this aspect, the z-axis of master grip 230 is on the roll axis and points away from the hand. The corresponding z-axis on the slave is, for example, along the centerline of the jaws and indicates where the jaws are pointing.

In one aspect, orientation 235 of master grip 230 in the common frame of reference is defined in teleoperation servo control system 160 by a master grip rotation matrix $R_m$, which in this example is a three-by-three matrix. Similarly, orientation 225 of slave surgical instrument tip 212T in the common frame of reference is defined in teleoperation servo control system 160 by a slave surgical instrument tip rotation matrix $R_s$, which in this example also is a three-by-three matrix. Master grip rotation matrix $R_m$ and slave surgical instrument tip rotation matrix $R_s$ are orthonormal rotation matrices.

With these matrix representations of orientations 235 and 225, the orientation error in the common frame of reference is a relative rotation matrix $R_\Delta$. Relative rotation matrix $R_\Delta$ is defined as:

$$R_\Delta = R_S^T * R_m \qquad (1)$$

where matrix $R_s^T$ is the transpose of slave surgical instrument tip rotation matrix $R_s$. It follows from the definitions of matrix $R_s^T$ and matrix $R_m$, taken with definition (1) that relative rotation matrix $R_\Delta$ is a three-by-three matrix:

$$R_\Delta = \begin{pmatrix} R_{\Delta 11} & R_{\Delta 12} & R_{\Delta 13} \\ R_{\Delta 21} & R_{\Delta 22} & R_{\Delta 23} \\ R_{\Delta 31} & R_{\Delta 32} & R_{\Delta 33} \end{pmatrix}$$

When orientation 235 of master grip 230 and orientation 225 of slave surgical instrument tip 212T are aligned in the common frame of reference, relative rotation matrix $R_\Delta$ is an identity matrix, i.e., diagonal elements $R_{\Delta 11}$, $R_{\Delta 22}$, $R_{\Delta 33}$ have a value of one and all other elements have a value of zero.

With these definitions of master grip rotation matrix $R_m$, slave surgical instrument tip rotation matrix $R_s$, and relative rotation matrix $R_\Delta$, subsequent master grip orientations are mapped to corresponding slave orientation commands, in the common frame of reference, via:

$$R_S = R_m * R_\Delta^T \qquad (2)$$

where matrix $R_\Delta^T$ is the transpose of relative rotation matrix $R_\Delta$.

As described above, with a current relative rotation matrix $R_{\Delta\text{-}Current}$ and a new relative rotation matrix $R_{\Delta\text{-}New}$, a decision must be made on which of the two relative rotation matrices to use in the mapping to the corresponding slave orientation command. New relative rotation matrix $R_{\Delta\text{-}New}$ is used when $$R_{\Delta\text{-}New} < R_{\Delta\text{-}Current}$$

However, it has been recognized that a scalar quantity can be used to determine which relative rotation matrix to use. Thus, a technique for comparing multi-dimension matrices is not needed to determine when new relative rotation matrix $R_{\Delta\text{-}New}$ is less than current relative rotation matrix $R_{\Delta\text{-}Current}$.

Figure 2B:
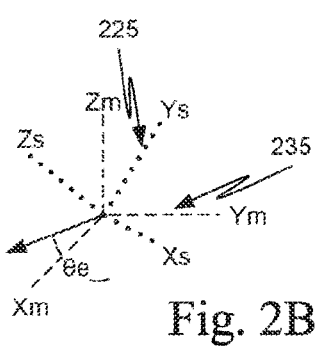
FIG. 2B illustrates the orientations of the master grip and the slave grip and rotation angle error $\theta_e$ between the two orientations.

As illustrate in FIG. 2B, the orientation error between orientation 235 of master grip 230 and orientation 225 of slave surgical instrument tip 212T, in the common frame of reference, is represented by a scalar rotation angle error $\theta_e$. Rotation angle error $\theta_e$ is the angle through which slave surgical instrument tip orientation 225 must be rotated to coincide with master grip orientation 235 and so represents the misalignment.

Rotation angle error $\theta_e$ is defined as:

$$\theta_e = \cos^{-1}[0.5 * (R_{\Delta 11} + R_{\Delta 22} + R_{\Delta 33} - 1)] \qquad (3)$$

Recall, as described above, when master grip orientation 235 and slave surgical instrument tip orientation 225 are aligned, diagonal elements $R_{\Delta 11}$, $R_{\Delta 22}$, $R_{\Delta 33}$ have a value of one. Thus, when the two orientations are aligned, rotation angle error $\theta_e$ is zero.

Figure 4A:
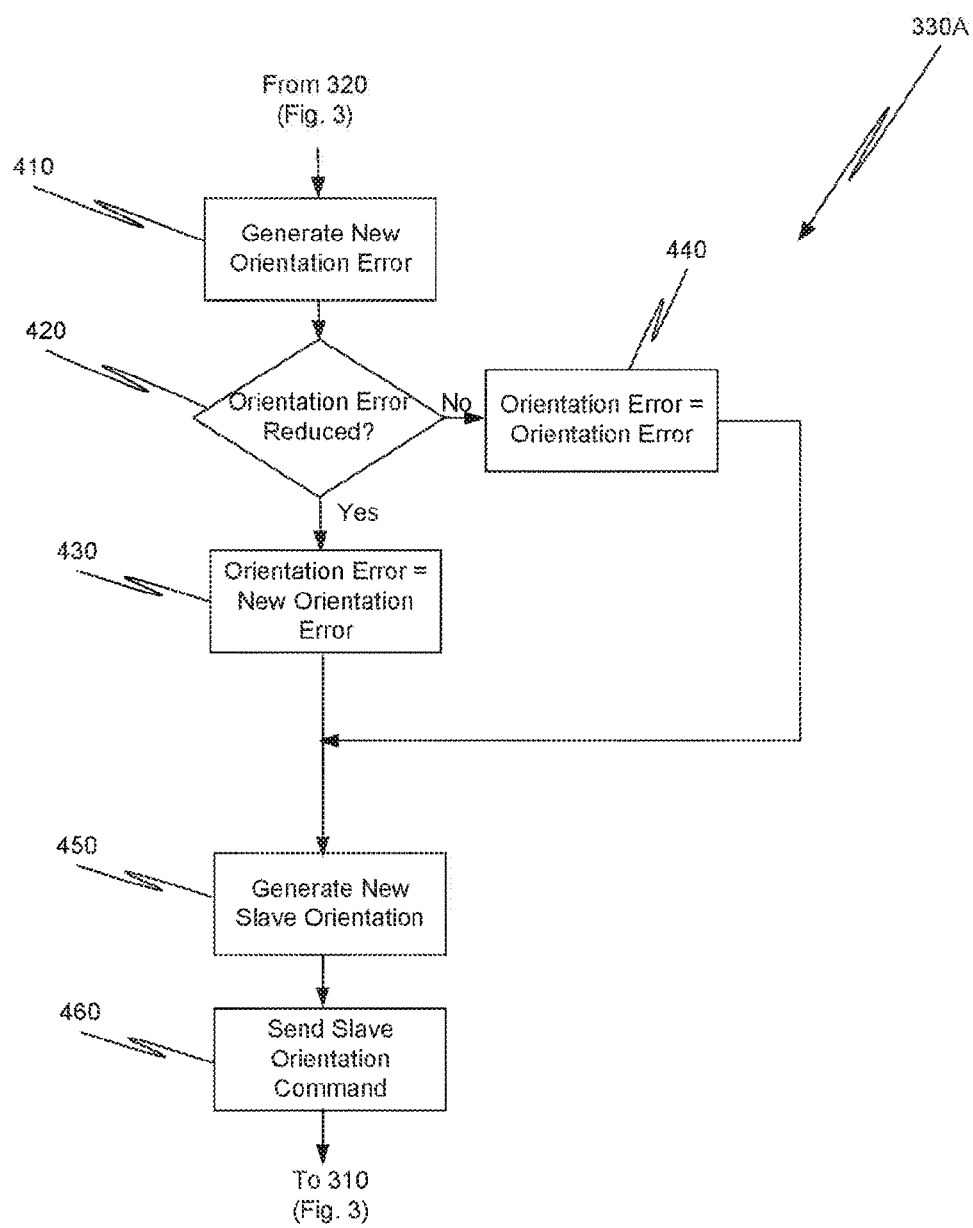
FIG. 4A is a process flow diagram for one aspect of the ratchet alignment process of FIG. 3A.
Figure 4B:
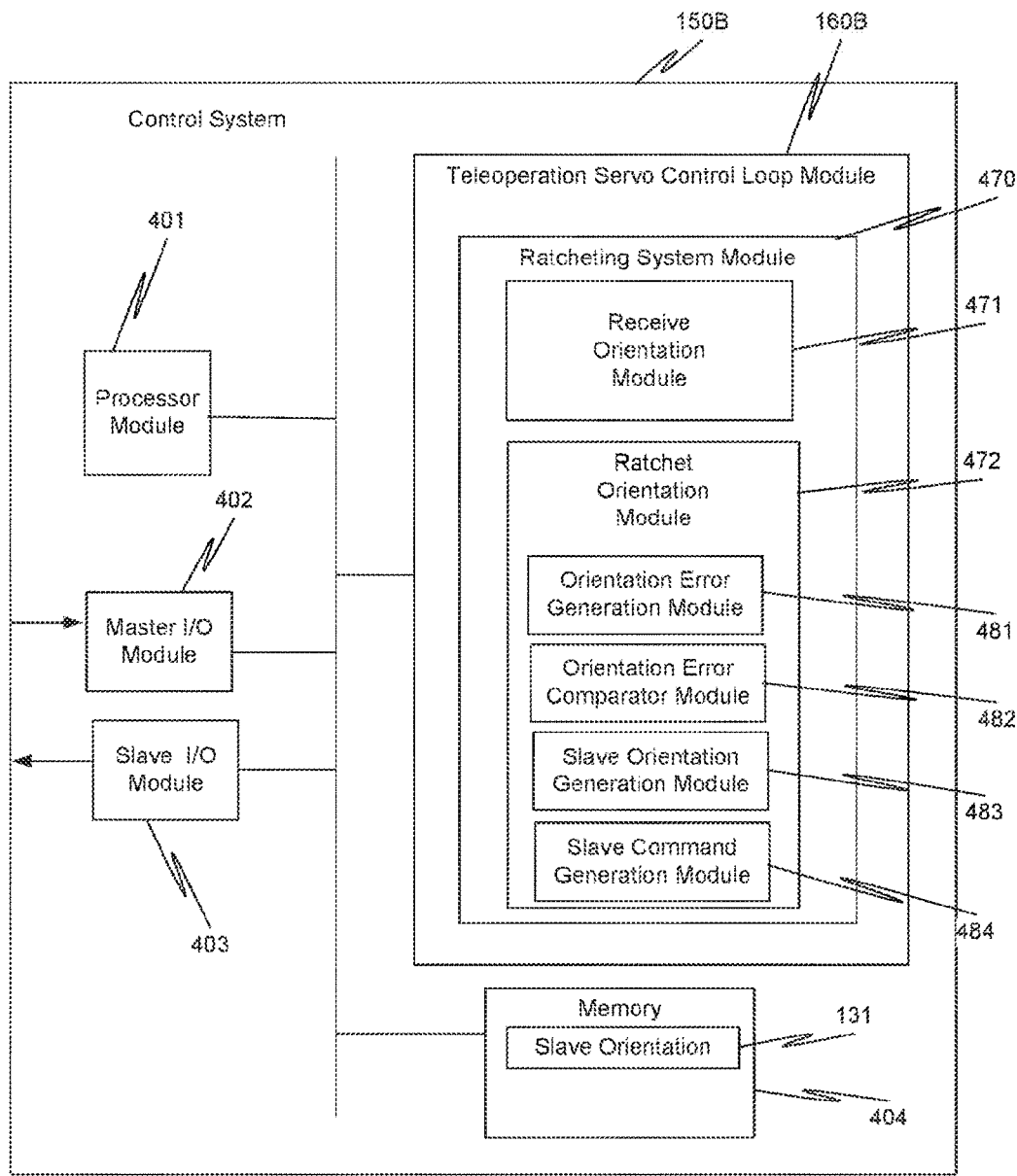
FIG. 4B is a block diagram of a control system including the modules used to implement the ratchet alignment process.

In this aspect, ratchet alignment process 330 for ratcheting system 130 is implemented as ratchet orientation process 330A (FIG. 4A) in association with a ratcheting system module 470. Ratcheting system module 470 includes a receive orientation module 471 and a ratchet orientation module 472 (FIG. 4B).

Upon entering following, generate new orientation error process 410, which is associated with orientation error generation module 481, accesses master grip rotation matrix $R_m$ and slave surgical instrument tip rotation matrix $R_s$.

Next, process 410 uses master grip rotation matrix $R_m$ and slave surgical instrument tip rotation matrix $R_s$ to generate a new relative rotation matrix $R_{\Delta\text{-}New}$ based on definition (1) above. Here, slave surgical instrument tip rotation matrix $R_s$ is the current orientation of slave surgical instrument tip 212T and is stored for example, in slave orientation element 131 in memory 404 (FIG. 4B), while master grip rotation matrix $R_m$ is a new orientation of master grip 230. The diagonal elements of new relative rotation matrix $R_{\Delta\text{-}New}$ are used in definition (3) above to generate a new rotation angle error $\theta_{e\text{-}New}$. After generation of new rotation angle error $\theta_{e\text{-}New}$, process 410 transfers to orientation error reduced check operation 420 that is associated with orientation error comparator module 482 (FIG. 4B).

Orientation error reduced check operation 420 determines whether new rotation angle error $\theta_{e\text{-}New}$ is less than current rotation angle error $\theta_{e\text{-}Current}$, e.g., check operation 420 is implemented as a comparator. If new rotation angle error $\theta_{e\text{-}New}$ is equal to or greater than current rotation angle error $\theta_{e\text{-}Current}$, check operation 420 passes to set orientation operation 440. Conversely, if new rotation angle error $\theta_{e\text{-}New}$ is less than current rotation angle error $\theta_{e\text{-}Current}$, check operation passes processing to set orientation operation 430.

The use of two set orientation operations 430, 440 is for ease of illustration only and is not intended to be limiting. A single set orientation operation could be used for the instances in which rotation angle error $\theta_e$ is reduced, for example. Also, note that in the first pass through ratchet orientation process 330A, check operation 420 may simply pass processing to set orientation error operation 430. Alternatively, in initialization, current rotation angle error $\theta_e$-Current can be set to a large value so that new rotation angle error $\theta_{e\text{-}New}$ is always less than current rotation angle error $\theta_{e\text{-}Current}$ in the first pass. The particular aspect used to handle the first pass through process 330A is not critical so long as no autonomous motion is introduced.

Set orientation error operation 440 is effectively a no-op, because current rotation angle error $\theta_{e\text{-}Current}$ and current relative rotation matrix $R_{\Delta\text{-}Current}$ are maintained as the current rotation angle error and the current relative rotation matrix, respectively. Thus, operation 440 can be removed and processing simply transfers from check operation 420 directly to generate new slave orientation 450.

Set orientation error operation 430, which is associated with comparator module 482, sets current rotation angle error $\theta_{e\text{-}Current}$ to new rotation angle error $\theta_{e\text{-}New}$. Operation 430 also sets current relative rotation matrix $R_{\Delta\text{-}Current}$ to new relative rotation matrix $R_{\Delta\text{-}New}$ and then transfers to generate new slave orientation operation 450.

Generate new slave orientation 450, which is associated with slave generation orientation module 483, first generates a transpose matrix $R_\Delta^T$ of current relative rotation matrix $R_{\Delta\text{-}Current}$. Next, a new slave orientation matrix $R_s$ is obtained by combining transpose matrix $R_\Delta^T$ and master grip rotation matrix $R_m$ according to definition (2), above. Thus, operation 450 transforms the master orientation into a slave orientation.

Generate new slave orientation 450 transfers processing to send slave orientation command operation 460, which is associated with slave command generation module 484. Using new slave orientation $R_s$, operation 460 sends a command, via slave input/output (I/O) module 403, which results in slave surgical instrument tip 212T being moved. The movement depends upon which relative rotation matrix $R_\Delta$ was used in the current iteration of process 330A.

In process 330A, When the surgeon moves master grip 230 in a way that reduces the alignment error in the common reference frame between master grip 230 and slave surgical instrument tip 212T, e.g., reduces rotation angle error $\theta_e$, ratchet alignment process 330A (FIG. 4A) uses the reduced alignment error in the following between master grip 230 and slave surgical instrument tip 212T. Conversely, when the surgeon moves master grip 230 in a way that increases the alignment error in the common reference frame between master grip 230 and slave surgical instrument tip 212T, ratchet alignment process 330A uses the current alignment error, and not the increased alignment error, in the following between master grip 230 and slave surgical instrument tip 212T.

Thus, ratchet alignment process 330A seamlessly and continuously improves the absolute alignment of master grip 230 with respect to slave surgical instrument tip 212T. Ratchet alignment process 330A achieves the continuous improvement in absolute alignment without autonomous motion of either master grip 230 or slave surgical instrument tip 212T.

If master grip 230 and the slave surgical instrument tip were rigidly connected, relative rotation matrix $R_\Delta$ would be a constant. In reality, master grip 230 and the slave surgical instrument tip are not rigidly connected, but are coupled through teleoperation servo control system 160. Whenever master grip 230 and the slave surgical instrument tip are in motion, there is always a small amount of control error. This control error can be absorbed using process 330A and alignment obtained between master grip 230 and slave surgical instrument tip 212T.

However, this approach is highly dependent on the stiffness of the servo control loop. Under normal conditions in a teleoperated minimally invasive surgical system with a stiff servo control loop, the incremental improvements may be too small and thus take a long time to reach satisfactory alignment. Even in such systems, ratcheting system 130 is still used, but an introduce control system error controller 560 (FIG. 5A) introduces a subtle control error between master grip orientation 235 and slave surgical instrument tip orientation 225, in the common frame of reference, without resulting in autonomous motion of slave surgical instrument tip.

Techniques for introducing such a subtle control error by introduce control system error controller 560 include, but are not limited to:

1. Penalizing slave angular velocity based on the amount of rotation angle error $\theta_e$. This introduces control error by artificially slowing down motion of the slave based on rotation angle error $\theta_e$.
2. Imposing artificial joint limits on the motion of slave surgical instrument tip rotation matrix $R_s$, when rotation angle error $\theta_e$ is greater than a permissible threshold. This results in control error between master and slave whenever the slave reaches an artificial joint limit. The permissible range of motion for the slave can be gradually widened to the full range of slave motion as alignment improves.
3. Low-pass filtering the sensed master grip rotation matrix $R_m$. This permits control error to be induced and absorb fast and/or discontinuous motions of master grip 230. The low-pass filter cutoff may be a function of rotation angle error $\theta_e$, such that responsiveness improves as rotation angle error $\theta_e$ decreases.
4. Low-pass filtering the commanded slave surgical instrument tip rotation matrix $R_s$. This introduces control error between master grip 230 and slave surgical instrument tip 212T, which can absorb fast and/or discontinuous orientation commands of slave surgical instrument tip 212T. The low-pass filter cutoff may be a function of rotation angle error $\theta_e$, such that responsiveness improves as rotation angle error $\theta_e$ decreases.

Figure 5A:
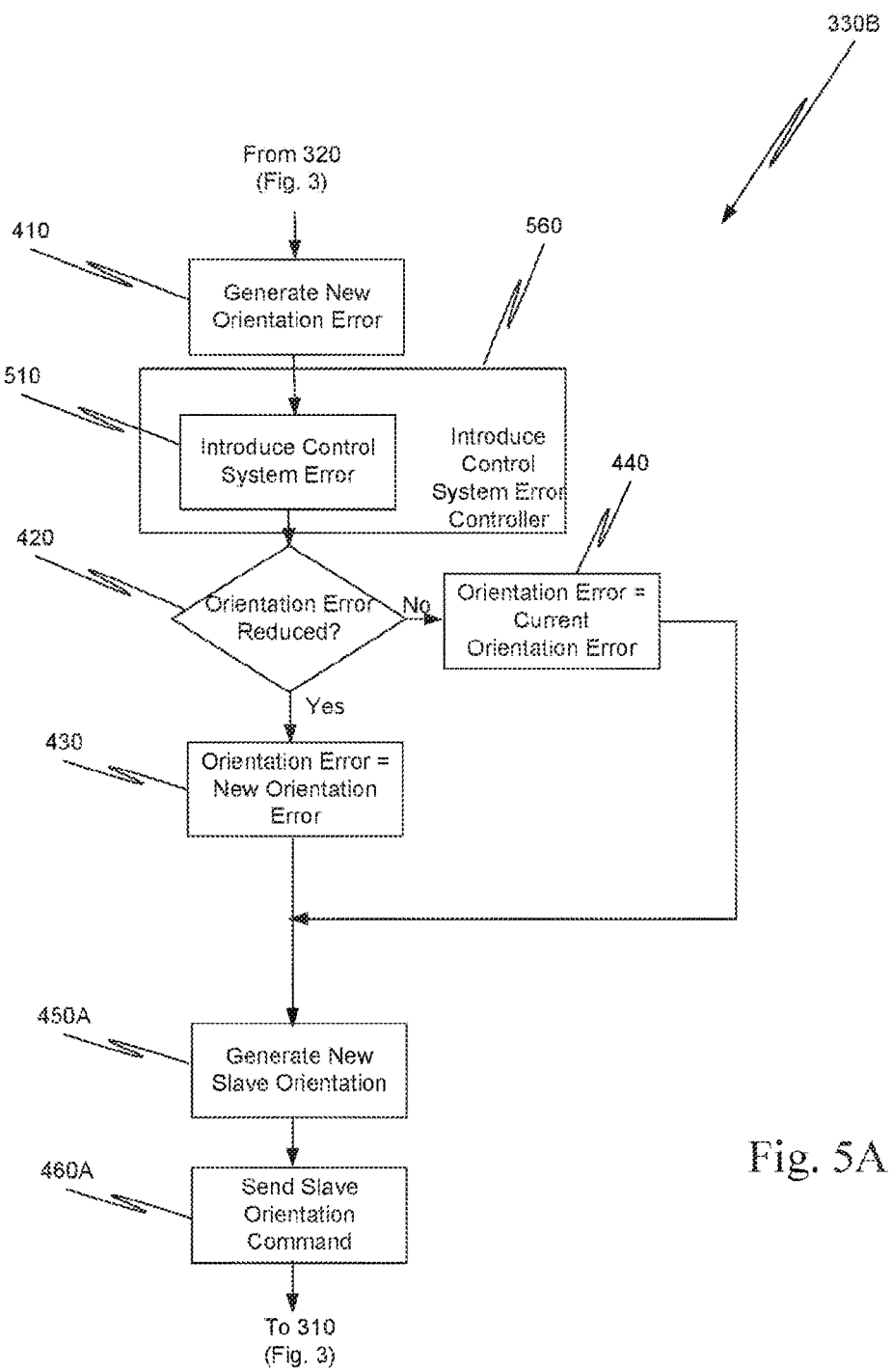
FIG. 5A is a process flow diagram for another aspect of the ratchet alignment process of FIG. 3A.

FIG. 5A illustrates another implementation of ratchet orientation process 330B in ratcheting system 130. Ratchet orientation process 330B uses one of the above techniques or another equivalent technique to introduce a control system error between the orientations of the slave surgical instrument tip and the master grip, in the common frame of reference, via introduce control system error process 510. The other processes 410, 420, 430, 440, 450A and 460A are similar to the corresponding process described above with respect to FIG. 4A and so that description is not repeated.

In this example, introduce control system error operation 510 in controller 560 introduces the control system error after generation of new rotation angle error $\theta_{e-New}$ in process 410. This location in process 330B is illustrative only and is not intended to be limiting to this specific location in process 330B. Upon selection of a particular technique to introduce control system error, introduce control system error operation 510 can be placed at an appropriate position within process 330B. Also, an introduce control system error module is included within ratchet orientation module 472 (FIG. 4B) in this example.

In one aspect, operation 510 introduces control error by artificially adjusting the commanded angular velocity of the slave surgical instrument tip based on current rotation angle error $\theta_{e-Current}$. Many different techniques can be used for penalizing the commanded angular velocity.

In one aspect of operation 510, current rotation angle error $\theta_{e-Current}$ is used in combination with an angular velocity penalty profile to generate an angular velocity scale factor for penalizing the commanded angular velocity of the slave instrument tip. In this aspect the angular velocity scale factor varies between zero for unacceptable rotation angle errors and one for a rotation angle error of zero.

The angular velocity may be penalized using an angular velocity penalty profile which smoothly varies between zero and one as rotation angle error $\theta_e$ changes. More generally, any continuous and monotonic angular velocity penalty profile can be used so long as the profile does not introduce autonomous motion and does not produce unexpected movement of the slave tip. As used here, continuous means that the first derivative of the profile exists at any point in the profile.

In one aspect, an angular velocity penalty profile is selected based on the experience of the surgeon. In another aspect, a single angular velocity penalty profile is used for all surgeons. In still yet another aspect, the angular velocity penalty profile is surgeon specific.

Figure 5B:
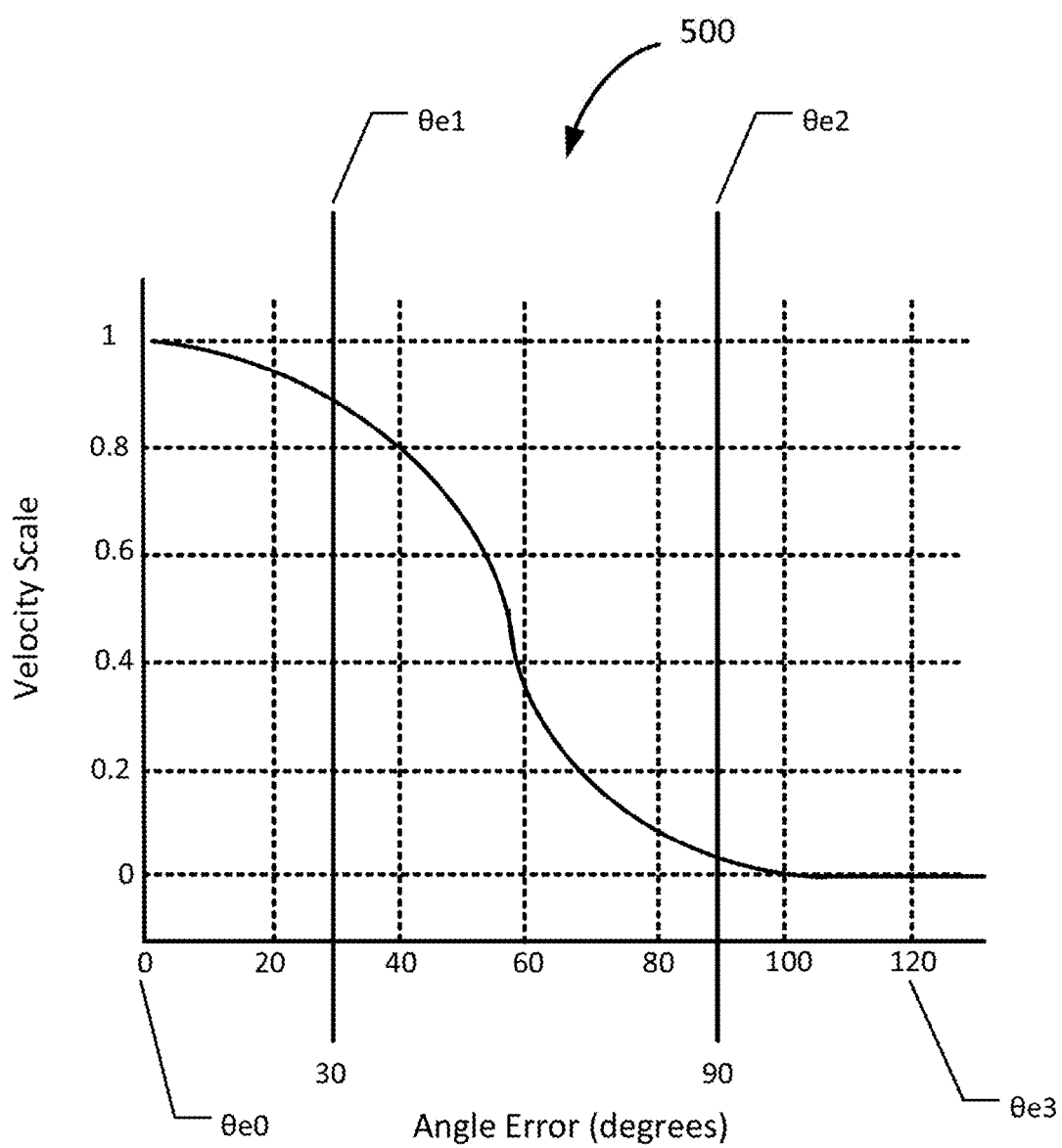
FIG. 5B is an illustration of an angular velocity penalty profile.

One angular velocity penalty profile suitable for use is a sigmoid shape curve. FIG. 5B depicts an angular velocity penalty profile 500 that is a sigmoid shape curve with two distinct inflection points $\theta_{e1}$ and $\theta_{e2}$, respectively.

In this example, first inflection point $\theta_{e1}$ is placed at 30 degrees and second inflection point $\theta_{e2}$ is placed at 90 degrees. Angle $\theta_{e0}$ is the angle at which the weight, more specifically referred to as the angular velocity scale factor, is a one, while angle $\theta_{e3}$ is the angle at which the weight becomes zero and remains zero for any larger misalignments.

The misalignment angle associated with inflection point $\theta_{e1}$ is selected to represent the user tolerance to misalignment, whereas the misalignment angle associated with inflection point $\theta_{e2}$ is selected to represent a maximum usable misalignment angle so that angles larger than inflection point $\theta_{e2}$ are considered unusable alignments. Whenever rotation angle error $\theta_e$ is greater than inflection point $\theta_{e2}$, the commanded angular velocity of the slave surgical instrument tip is scaled towards zero, which results in little or no motion of the slave surgical instrument tip. This allows relative rotation matrix $R_\Delta$ to be readily updated as the operator rotates master grip 230 towards slave surgical instrument tip 212T.

As rotation angle error $\theta_e$ decreases towards inflection point $\theta_{e1}$, the commanded angular velocity is gradually increased, allowing for more responsive motion of the slave surgical instrument tip while still inducing enough control error to further improve relative rotation matrix $R_\Delta$. Once rotation angle error $\theta_e$ becomes less than inflection point $\theta_{e1}$, slave surgical instrument tip 212T is perceived by the surgeon to be well aligned with master grip 230. Therefore, the angular motion of the slave surgical instrument tip 212T is allowed to be more responsive to the motion of master grip 230. Additional small alignment corrections continue to be made until relative rotation matrix $R_\Delta$ becomes the identity matrix and rotation angle error $\theta_e$ goes to zero.

With respect to artificial joint limits, artificial joint limits on slave motion are defined as a function of the alignment error in the common frame of reference, e.g., as a function of rotation angle error $\theta_e$. When the alignment error is large, e.g., greater than ninety degrees, artificial joint limits are imposed on motion of slave surgical instrument tip 212T that allow instrument tip 212T to make small motions about the current position of instrument tip 212T.

As master grip 230 moves towards slave surgical instrument tip 212T, slave surgical instrument tip 212T moves in the same relative direction until an artificial joint limit is encountered. When an artificial joint limit is encountered, slave surgical instrument tip 212T remains fixed in position at the artificial joint limit. This allows ratcheting system 130 to aggressively reduce the alignment error as master grip 230 continues to move in the direction of slave surgical instrument tip 212T.

In one aspect, the artificial joint limits are gradually widened as the alignment error decreases. This makes the alignment process more seamless and continuous.

If, for example, low-pass filtering of the sensed master grip rotation matrix $R_m$ is used to introduce a control system error, master grip rotation matrix $R_m$ changes at a lower frequency. For example, humans can make controlled motions up to around 20 Hz. The master orientation can be aggressively filtered down, e.g. to one to five Hertz, to make the orientation changes more sluggish when alignment is poor. Again, a monotonic penalty profile could be used to move between zero Hertz and twenty Hertz as a function of the current orientation error.

Conversely, if, for example, low-pass filtering of commanded slave surgical instrument tip rotation matrix $R_s$ is used to introduce a control system error, slave surgical instrument tip rotation matrix $R_s$ changes at a lower frequency. In view of these examples, one knowledgeable in the field can select an appropriate low-pass filter so that the ratcheting seamlessly and continuously improves the absolute alignment of master grip 230 with respect to slave surgical instrument tip 212T. Ratchet alignment process 330B achieves the continuous improvement in absolute alignment without autonomous motion of either master grip 230 or slave surgical instrument tip 212T.

Figure 6A:
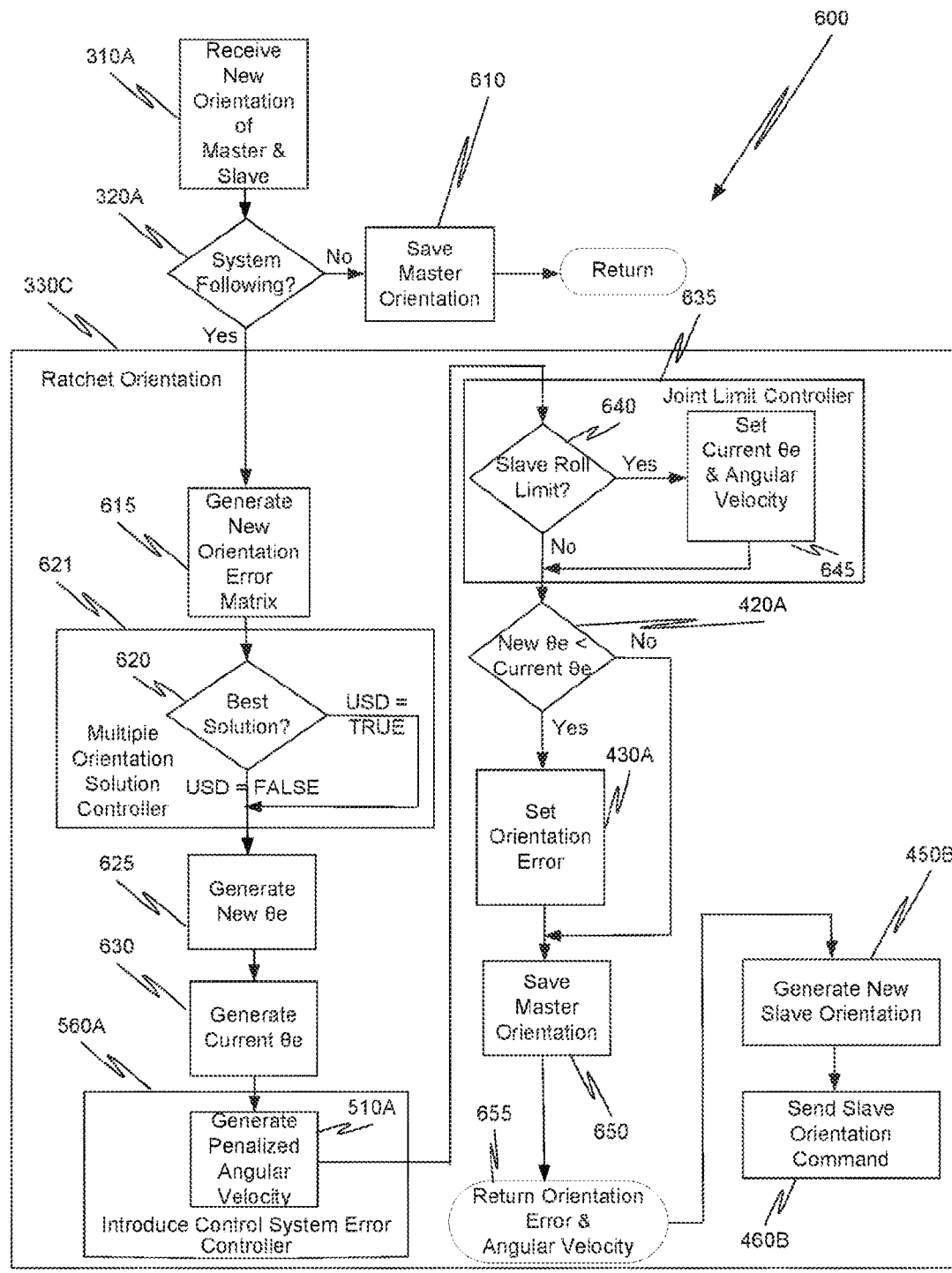
FIG. 6A is a process flow diagram for another aspect of the ratcheting system.
Figure 6B:
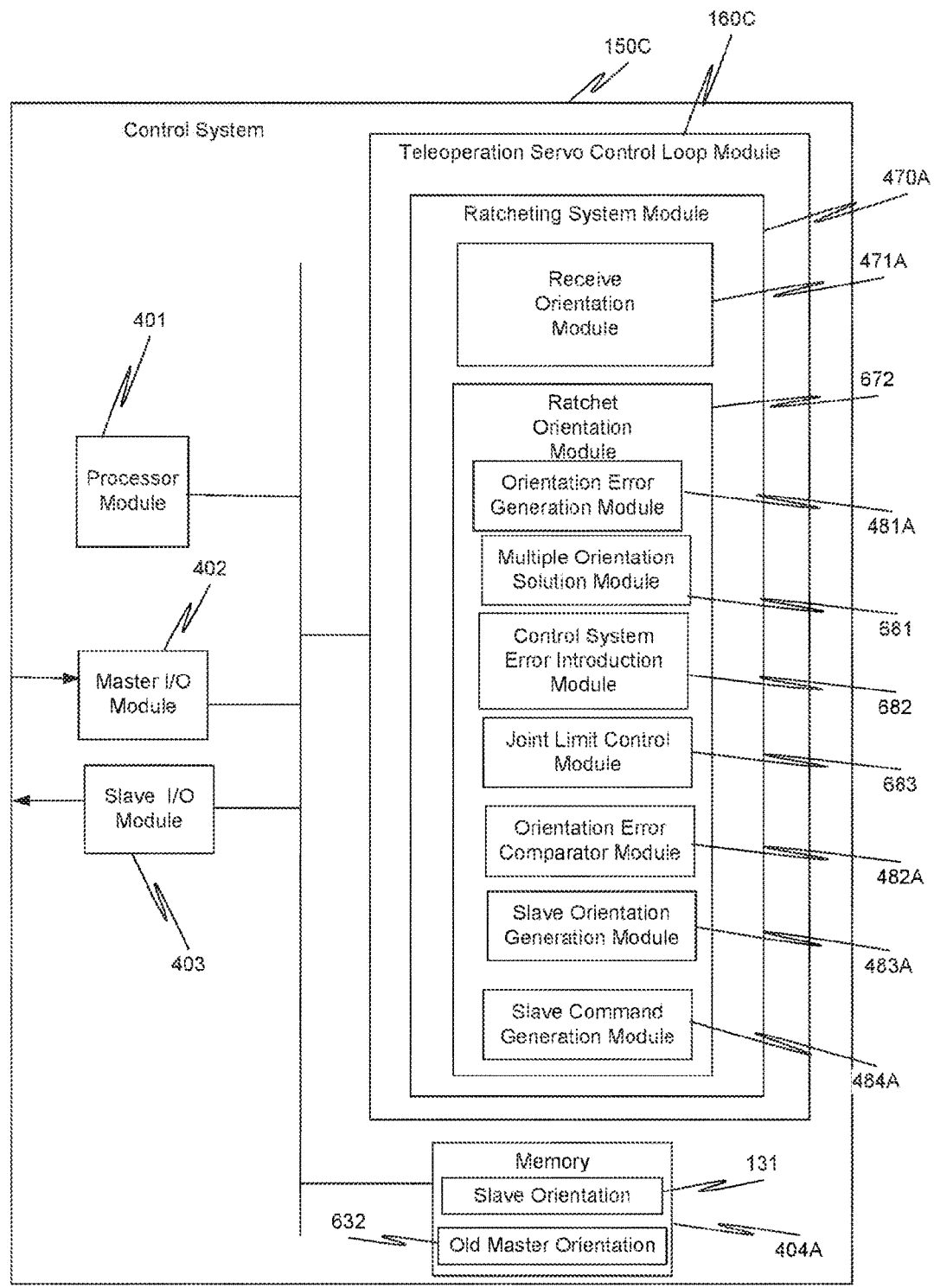
FIG. 6B is a block diagram of control system including the modules used to implement the ratcheting system of FIG. 6A.

In another aspect, method 600 (FIG. 6A) is performed by ratcheting system 130. In this aspect, ratcheting system 130 includes a ratcheting system module 470A (FIG. 6B). Ratcheting system module 470A includes a receive orientation module 471A and ratchet orientation module 672. As explained more completely below, ratchet orientation process 330C (FIG. 6A), which is associated with ratchet orientation module 672, penalizes slave angular velocity based on the magnitude of rotation angle error $\theta_e$; includes a roll joint limit controller; and determines how a surgeon has grasped master grip 230, e.g., right side up or upside down.

Receive new orientation of master and slave operation 310A, associated with receive orientation module 471A, receives master grip orientation 235 and slave surgical instrument tip orientation 225. Operation 310A transfers to check operation 320A.

System following check operation 320A determines whether system following has been initiated. If system following has not been initiated, save master orientation operation 610 saves the received master orientation in old master orientation storage location 632 in memory 404A and processing is returned from the ratcheting system. Thus, until following is initiated, the ratcheting system maintains the most recent orientation of master grip 230 in the common frame of reference.

When system following is initiated, check operation 320A transfers to generate new orientation error matrix operation 615, which is associated with orientation error generation module 481A (FIG. 6B) in ratchet orientation module 672. Operation 610 uses master grip rotation matrix $R_m$ and slave surgical instrument tip rotation matrix $R_s$ to generate a new relative rotation matrix $R_{\Delta\text{-}New}$ based on definition (1) above. Here, slave surgical instrument tip rotation matrix $R_s$ is the current orientation of slave surgical instrument tip 212T in the common frame of reference and is stored for example, in slave orientation element 131 of memory 404A (FIG. 6B), while master grip rotation matrix $R_m$ is a new orientation of master grip 230. Upon completion, operation 615 transfers to best solution check operation 620, which is associated with multiple orientation solution module 681 in ratchet orientation module 672.

Best solution check operation 620 determines which of a set of multiple solutions for the orientation best matches the current orientation of master grip 230 in the common frame of reference. For example, with respect to the orientation of how the surgeon grasped master grip 230, two possible solutions are considered, right side up and upside down (USD). Thus, in one aspect, check operation 620 is implemented in a multiple orientation solution controller 621 that includes an upside down (USD) controller.

Assuming the surgeon used her/his right hand to grasp master grip 230, when the thumb is on lever 231 (FIG. 2A) and the forefinger is on lever 232 so that a top of the surgeon's wrist is visible to the surgeon, this is referred to as right side up. Conversely, when the thumb is on lever 232 and the forefinger is on lever 231 so that a bottom of the surgeon's wrist is visible to the surgeon, this is referred to as upside down. Thus, the two solutions for the grasping orientation are 180° apart along the roll axis. To determine which of the two orientation solutions to use in process 330C, the cosine of rotation angle error $\theta_e$ is determined for each of the orientations. If the cosine for the upside down orientation is larger than the cosine for the right side up orientation, the upside down orientation is set to true and otherwise is set to false.

Thus, using definition (3) above, in one aspect, check operation 620 performs the following operations:

$$\cos(\theta_e\_s) = [0.5 * (R_{\Delta 11} + R_{\Delta 22} + R_{\Delta 33} - 1)]$$

$$\cos(\theta_e\_f) = [0.5 * (-1 * R_{\Delta 11} - R_{\Delta 22} + R_{\Delta 33} - 1)]$$

The orientation in the two dimensions is upside down when $\cos(\theta_e\_f)$ is greater than $\cos(\theta_e\_s)$ and upside-down orientation flag USD is set to true. Conversely, when $\cos(\theta_e\_f)$ is less than or equal to $\cos(\theta_e\_s)$, upside-down orientation flag USD is set to false.

Generate new rotation angle error $\theta_e$ operation 625 and generate current rotation angle error $\theta_e$ operation 630 are associated with orientation error generation module 481A. Operations 625 and 630 generate a new rotation angle error $\theta_{e\text{-}New}$ and a current rotation angle error $\theta_{e\text{-}Current}$ using the state of upside down orientation flag USD, a new relative rotation matrix $R_{\Delta\text{-}New}$, and a current relative rotation matrix $R_{\Delta\text{-}Current}$.

Specifically, if upside-down orientation flag USD is set to true, operation 625 first rotates current relative rotation matrix $R_{\Delta\text{-}Current}$ in the two dimensions, and then determines current rotation angle error $\theta_{e\text{-}Current}$, as explained above. If upside-down orientation flag USD is set to false, operation 625 determines current rotation angle error $\theta_{e\text{-}Current}$ without any rotation. Current rotation angle error $\theta_{e\text{-}Current}$ is checked and (1) if the value is greater than pi, current rotation angle error $\theta_{e\text{-}Current}$ is set to pi, or (2) if the value is less than zero, current rotation angle error $\theta_{e\text{-}Current}$ is set to zero. Thus, current rotation angle error $\theta_{e\text{-}Current}$ is bounded between zero and pi.

Similarly, if upside-down orientation flag USD is set to true, operation 630 first rotates new relative rotation matrix $R_{\Delta\text{-}New}$ in the two dimensions, and then determines new rotation angle error $\theta_{e\text{-}New}$, as explained above. If upside-down orientation flag USD is set to false, operation 630 determines new rotation angle error $\theta_{e\text{-}New}$ without any rotation. New rotation angle error $\theta_{e\text{-}New}$ is checked and (1) if the value is greater than pi, new rotation angle error $\theta_{e\text{-}New}$ is set to pi, or (2) if the value is less than zero, new rotation angle error $\theta_{e\text{-}New}$ is set to zero. Thus, new rotation angle error $\theta_{e\text{-}New}$ also is bounded between zero and pi.

Following the determination of the rotation angle errors in operations 625 and 630 based on the best solution, a control system error is introduced in generate penalized angular velocity operation 510A, which is associated with control system error introduction module 682 in ratchet orientation module 672 (FIG. 6B).

In this aspect, operation 510A is implemented in an introduce control system error controller 560A, which in turn is associated with control system error introduction module 682. Penalizing the angular velocity is an example of a one type of control system error that can be introduced by introduce control system error controller 560A. In general, introduce control system error controller 560A introduces a control error, such as those described above.

In this aspect of generate penalized angular velocity operation 510A, the angular velocity is penalized by multiplying the angular velocity sensed from master grip 230 by the angular velocity scale factor from penalty curve 500 based on current rotation angle error $\theta_{e\text{-}Current}$, as described above. Following completion of operation 510A, processing transfers to joint limit control process, which is implemented in a roll-joint limit controller 635. Roll-joint limit controller 635 is associated with joint limit control module 683 in ratchet orientation module 672.

Roll-joint limit controller 635 determines whether a slave surgical instrument joint has reached a limit in a given direction and whether the sensed motion from master grip 230 is trying to move the slave surgical instrument tip in that given direction. In this aspect, slave roll limit check operation 640, in roll-joint limit controller 635, determines whether the roll joint in the slave surgical instrument has reached a roll limit, and if the sensed motion from master grip 230 is trying to rotate slave surgical instrument tip 212T in that roll direction.

In check operation 640, the upper and lower roll limits are predefined. Old master grip rotation matrix $R_{m\text{-}old}$, which was stored in old master orientation location 632, is transposed. A relative master grip rotation matrix $R_{m\Delta}$ is defined as:

$$R_{m\Delta} = R_{m\text{-}old}^T * R_m$$

Thus, relative master grip rotation matrix $R_{m\Delta}$ is a three-by-three matrix:

$$R_{m\Delta} = \begin{pmatrix} R_{m\Delta 11} & R_{m\Delta 12} & R_{m\Delta 13} \\ R_{m\Delta 21} & R_{m\Delta 22} & R_{m\Delta 23} \\ R_{m\Delta 31} & R_{m\Delta 32} & R_{m\Delta 33} \end{pmatrix}$$

The master grip roll direction is defined as:

$$\text{Master\_roll\_dir} = [R_{\Delta 21} - R_{\Delta 12}].$$

Next, check operation 640 determines first whether the position of slave surgical instrument tip 212T is less than the lower roll joint limit plus a tolerance and master roll direction Master_roll_dir is less than zero. If the result of this first determination is true, the lower roll joint limit has been reached and the direction of the master grip rotation is in the direction of that lower roll limit. Thus, the slave surgical instrument tip motion is constrained.

If the result of this first determination is false, check operation 640 determines second whether the position of the slave surgical instrument tip is greater than the upper roll joint limit minus a tolerance and master roll direction Master_roll_dir is greater than zero. If the result of this second determination is true, the upper roll joint limit has been reached and the direction of the master grip rotation is in the direction of that upper roll limit. Thus, the slave surgical instrument motion is constrained.

When the slave surgical instrument motion is constrained, slave roll limit check operation 640 transfers to set current rotation angle error and angular velocity operation 645, and otherwise to rotation angle error reduced check operation 420A. Set current rotation angle error and angular velocity operation 645 sets current rotation angle error $\theta_{e\text{-}Current}$ to a value larger than any possible physical value, and sets the commanded angular velocity to zero. Set current rotation angle error and angular velocity operation 645 transfers processing to orientation error reduced check operation 420A.

Orientation error reduced check operation 420A determines whether new rotation angle error $\theta_{e\text{-}New}$ is less than current rotation angle error $\theta_{e\text{-}Current}$, e.g., check operation 420 is implemented as a comparator. If new rotation angle error $\theta_{e\text{-}New}$ is equal to or greater than current rotation angle error $\theta_{e\text{-}Current}$, check operation 420A passes to save master orientation operation 650. Conversely, if new rotation angle error $\theta_{e\text{-}New}$ is less than current rotation angle error $\theta_{e\text{-}Current}$, check operation 420A passes processing to set orientation error operation 430A.

Set orientation error operation 430A, which is associated with comparator module 482A, sets current rotation angle error $\theta_{e\text{-}Current}$ to new rotation angle error $\theta_{e\text{-}New}$. Operation 430A also sets current relative rotation matrix $R_{\Delta\text{-}Current}$ to new relative rotation matrix $R_{\Delta\text{-}New}$ and then transfers to save master orientation operation 650, which saves master grip rotation matrix $R_m$ in element 632 (FIG. 6B). Operation 650 transfers processing to generate new slave orientation operation 450B (FIG. 6A).

Generate new slave orientation 450B, which is associated with slave generation orientation module 483A (FIG. 6B), first generates a transpose matrix $R_\Delta^T$ of current relative rotation matrix $R_{\Delta\text{-}Current}$. Next, a new slave orientation matrix $R_s$ is obtained by combining transpose matrix $R_A{}^T$ and master grip rotation matrix $R_m$ according to definition (2), above.

Generate new slave orientation 450B transfers processing to send slave orientation command operation 460B (FIG. 6A), which is associated with slave command generation module 484A. Using new slave orientation $R_s$, operation 460 sends a command including the slave orientation and the commanded angular velocity, in the common frame of reference, via slave input/output (I/O) module 403, which results in slave surgical instrument tip 212T being moved as directed by that command. The movement depends upon which relative rotation matrix $R_A$ was used in the current iteration of process 330C and the commanded angular velocity.

When the surgeon moves master grip 230 in a way that reduces the alignment error between master grip 230 and slave surgical instrument tip 212T, e.g., reduces rotation angle error $\theta_e$, ratchet alignment process 330C (FIG. 6A) uses the reduced alignment error in the following between master grip 230 and slave surgical instrument tip 212T while accounting for how the surgeon grasped master grip 230 and whether a roll joint limit was encountered. Conversely, when the surgeon moves master grip 230 in a way that increases the alignment error between master grip 230 and slave surgical instrument tip 212T, ratchet alignment process 330C uses the current alignment error, and not the increased alignment error, in the following between master grip 230 and slave surgical instrument tip 212T.

Thus, ratchet alignment process 330C seamlessly and continuously improves the absolute alignment of master grip 230 with respect to slave surgical instrument tip 212T. Ratchet alignment process 330C achieves the continuous improvement in absolute alignment without autonomous motion of either master grip 230 or slave surgical instrument tip 212T.

Figure 7:
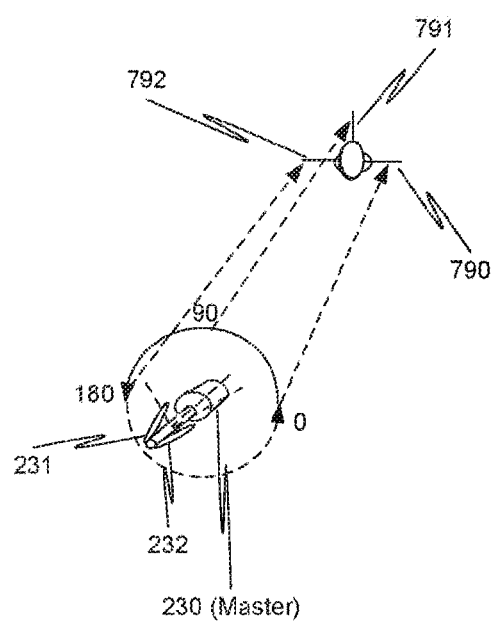
FIG. 7 is an illustration of corner-case handling of roll-joint limits for the slave surgical instrument tip.

In method 600, roll-joint limit controller 635 was used to handle a corner-case for a slave range of motion. This corner-case is considered further with respect to FIG. 7. FIG. 7 illustrates a technique for introducing corner-case joint limits. In this example, there is a roll joint limit at zero degrees and another roll joint limit at one hundred-eighty degrees. Thus, when master grip 230 is at zero degrees, slave surgical instrument tip is positioned as shown by slave surgical instrument tip 790; at ninety degree, slave surgical instrument tip is positioned as shown by slave surgical instrument tip 791; and at one hundred-eighty degrees, slave surgical instrument tip is positioned as shown by slave surgical instrument tip 792.

If the surgeon continued to rotate master grip 230 in the counter clockwise direction back to zero degrees, slave tip 792 suddenly might move to the orientation of slave tip 790, e.g., there would be autonomous motion. However, with corner-case joint limits on the motion of the slave surgical instrument tip such motion is inhibited. For example, when the orientation of master grip 230 comes within a predetermined tolerance of a joint limit, the commanded angular velocity of the slave surgical instrument tip is set to zero and current rotation angle error $\theta_{e\text{-}Current}$ is set to an artificially large number so that new relative rotation matrix $R_{A\text{-}New}$ is used. This essentially allows the master orientation to slip relative to the orientation of the slave surgical instrument tip when the slave surgical instrument tip is at a roll limit.

With a conventional powered master, the user would receive force feedback to indicate when a slave has reached a range of motion limit. With an unpowered master, a roll-joint limit controller, in the ratcheting system, can be used to maintain continuity of slave motion as the master drives the slave in and out of a joint limit.

In the above methods, various modules and operations and/or processes associated with those modules were described. The modules may be implemented in hardware, software that is executed on a processor, firmware or any combination of hardware, software or firmware.

When the modules include one or more instructions stored on a storage medium, the described operations and/or processes are the result of retrieval and execution of the one or more instructions on at least one processor in processor module 401 to obtain the transformation described. The particular modules described are illustrative only and are not intended to be limiting. In view of the disclosure, one knowledgeable in the field can combine modules together or separate a module into one or more additional modules as may be desired. Moreover while the modules are shown grouped in a common location this also is illustrative only.

TABLE 1 is an example of software instructions written in the C-programming language that when executed on a processor perform elements 302A, 610, 615, 620, 621, 625, 630, 510A, 560A, 635, 640, 645, 420A, 430A and 650.

TABLE 1

```
#define CLAMP(val,lo,hi) (MIN(MAX((val),(lo)),(hi)))
typedef FLOAT (*Matrix3x3Ptr)[3];
/******************************************************/
static FLOAT psm_io_rotation_angle(const Matrix3x3Ptr R,
                BOOLEAN USD)
{
  float traceR;
  float costheta;
  /* Account for USD configuration by applying
  rotation of 180 degrees Z */
  if (USD)
  {
    FLOAT Rtmp[3][3];
    static const FLOAT Rroll[3][3] =
    {
      { -1, 0, 0 },
      { 0, -1, 0 },
      { 0, 0, 1 }
    };
    Matrix_multiplyMatrixf(Rtmp, /* = */ R, 3, 3,
              /* x */ Rroll, 3, 3);
    traceR = Rtmp[0][0] + Rtmp[1][1] + Rtmp[2][2];
  }
```

TABLE 1-continued

```
    else
    {
      traceR = R[0][0] + R[1][1] + R[2][2];
    }
    costheta = 0.5f * (traceR - 1.0f);
    if (costheta > 1.0)
    {
      return 0.0;
    }
    else if (costheta < -1.0)
    {
      return M_PI;
    }
    else
    {
      return (FLOAT) acos(costheta);
    }
  }
}
/**********************************************/
INT psm_io_constrain_master_roll
  (const Matrix3x3Ptr Rm_old, const Matrix3x3Ptr Rm)
{
  static const FLOAT tolerance = 1.0f * M_PI / 180.0;
  FLOAT* const pos = Ptr(SYS_HW_JNTPOS, 0,
           PSM_JNT_POS_DOFS);
  float_par* lower = Ptr(PC_JI_IK_POSLOWERLIMIT, 0,
           PSM_JNT_POS_DOFS);
  float_par* upper = Ptr(PC_JI_IK_POSUPPERLIMIT, 0,
           PSM_JNT_POS_DOFS);
  FLOAT Rm_old_trans[3][3];
  FLOAT Rm_delta[3][3];
  FLOAT mtm_roll_dir;
  INT constrain_roll = 0;
  //Compute the error rotation as R2 w.r.t. R1.
  Matrix_transposef(Rm_old_trans, Rm_old, 3, 3);
  /* Rm_delta = Rm_old_trans' * Rm */
  Matrix_multiplyMatrixf(Rm_delta,
           /* = */ Rm_old_trans, 3, 3, /* x */ Rm, 3, 3);
  //Define the local error vector w.r.t. R1.
  mtm_roll_dir = Scalar_fsignf(Rm_delta[1][0] -
           Rm_delta[0][1]);
  //Check if the PSM roll joint has reached a limit and //if the MTM
  is trying to rotate in that roll //direction
  if (pos[PSM_RO] < (lower[PSM_RO] + tolerance)
      && mtm_roll_dir < 0)
  {
    constrain_roll = 1;
  }
  else if (pos[PSM_RO] > (upper[PSM_RO] - tolerance)
      && mtm_roll_dir > 0)
  {
    constrain_roll = 1;
  }
  return constrain_roll;
}
/**********************************************/
// Parameters used by sigmoid-shaped velocity weight
// function
#define SIGMOID_ALPHA 5.0f
#define SIGMOID_BETA  (0.3f*M_PI)
/**********************************************
* psm_io_ratchet_offset( ) *
* Conditionally updates the orientation offset *
* to improve the alignment between MTM and PSM *
**********************************************/
void psm_io_ratchet_offset(const Matrix3x3Ptr Rm,
           Matrix3x3Ptr Roff, FLOAT *rotvel)
{
  static FLOAT Rm_old[3][3];
  FLOAT Rs_trans[3][3];
  FLOAT Roff_new[3][3];
  FLOAT cur_offset;
  FLOAT new_offset;
  FLOAT cosangle_s, cosangle_f;
  FLOAT vel_weight;
  BOOLEAN USD = FALSE;
  Matrix3x3Ptr Rs = (Matrix3x3Ptr) Ptr(SYS_IO_OUT_CART,
           3, 9);
  if (Kernel_RobustBooleanIsFALSE
         (PSM_IO_FOLLOW_DATA_VALID))
```

TABLE 1-continued

```
{
   Matrix_copyf(Rm_old, Rm, 3, 3);
   return;
}
/* Update the relative rotation offset Roff between master and slave,
if the current offset is smaller */
Matrix_transposef(Rs_trans, Rs, 3, 3);
// Compute the offset between the new MTM and new PSM
/* Roff_new = Rs' * Rm */
Matrix_multiplyMatrixf(Roff_new, /* = */ Rs_trans,
        3, 3, /* x */ Rm, 3, 3);
// Determine whether to use the straight or
// upside-down solution
cosangle_s = (FLOAT)(0.5 * (Roff_new[0][0] +
        Roff_new[1][1] + Roff_new[2][2] - 1));
cosangle_f = (FLOAT)(0.5 * (-1 * Roff_new[0][0] -
        Roff_new[1][1] + Roff_new[2][2] - 1));
USD = (cosangle_f > cosangle_s) ? TRUE : FALSE;
new_offset = psm_io_rotation_angle(Roff_new, USD);
cur_offset = psm_io_rotation_angle(Roff, USD);
/* Reduce the angular velocity based on the current
 * amount of misalignment. We are using a sigmoid
 * function as the weight, since it provides a smooth
 * transition between full velocity and no velocity.
 * The curve has been tuned to falloff near 30
 * degrees and bottom out around 90 degrees */
vel_weight = 1.0f/(1.0f + exp(SIGMOID_ALPHA*
        (cur_offset-SIGMOID_BETA)));
vel_weight = CLAMP(vel_weight, 0.0f, 1.0f);
vector_scalef(rotvel, rotvel, vel_weight,
            CART_ORI_DOFS);
/* Constrain the MTM command if the PSM has hit a roll limit */
if (psm_io_constrain_master_roll(Rm_old, Rm))
{
   cur_offset = BIG_NUM;
   vector_setf(rotvel, 0, CART_ORI_DOFS);
}
/* Conditionally update the Roff offset if we've found a smaller relative rotation*/
if (new_offset < cur_offset)
{
   Matrix_copyf(Roff, Roff_new, 3, 3);
}
// Save the most recent Rm
Matrix_copyf(Rm_old, Rm, 3, 3);
}
```

Figure 2C:
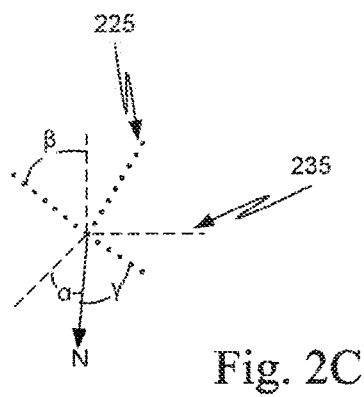
FIG. 2C illustrates the orientations of the master grip and the slave grip and the orientation error has been decomposed into a set of Euler angles.

In the examples of FIGS. 2B, 4A, 4B, 5A, 5B, 6A and 6B, a scalar quantity was used to determine the ratcheting of the orientation in three-dimensions in a common frame of reference. However, in another aspect, the scalar quantity can be associated with a single dimension in a common frame of reference. For example, instead of using scalar rotation angle error $\theta_e$ to specify the orientation error for three dimensions, relative rotation matrix $R_A$ can be decomposed in a set of Euler angles α, β, and γ (FIG. 2C). Line N represents the intersection of the two X-Y planes. In this instance, the ratcheting of processes 330, 330A, 330B, or 330C could be performed with respect to one of the Euler angles, e.g., Euler angle β, or the alignment error may be optimized by sequentially or concurrently ratcheting each of the Euler angles, or some subset of the set of Euler angles. For example, some minimally invasive surgical instruments could be constrained or implemented such that the orientation with respect to one of the Euler angles is of interest and so the ratcheting of the orientation would be done with respect to that Euler angle.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

While the memory is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of methods 300, 330, 330A, 330B, 600, 330C or in which computer readable code for any one or any combination of methods 300, 330, 330A, 330B, 600, 330C is stored. Some examples of computer program products are CD-ROM discs, DVD discs, flash memory, ROM cards, floppy discs, magnetic tapes, computer hard drives, servers on a network and signals transmitted over a network representing computer readable program code. A tangible computer program product comprises a medium configured to store computer readable instructions for any one of, or any combination of methods 300, 330, 330A, 330B, 600, 330C or in which computer readable instructions for any one of, or any combination of methods 300, 330, 330A, 330B, 600, 330C is stored. Tangible computer program products are CD-ROM discs, DVD discs, flash memory, ROM cards, floppy discs, magnetic tapes, computer hard drives and other physical storage mediums.

In view of this disclosure, instructions used in any one of, or any combination of methods 300, 330, 330A, 330B, 600, 330C can be implemented in a wide variety of computer system configurations using an operating system and computer programming language of interest to the user.

Further, various different minimally invasive systems and methods can be implemented in view of this disclosure.

In one aspect, a minimally invasive surgical system comprises:
  a slave surgical instrument having a slave surgical instrument tip wherein the slave surgical instrument tip has an alignment in a common coordinate frame of reference;
  a master grip, coupled to the slave surgical instrument, having an alignment in the common coordinate frame of reference,
    wherein an alignment error in the common frame of reference is a difference in alignment in the common frame of reference between the alignment of the slave surgical instrument tip and the alignment of the master grip; and
  a ratcheting system, (i) coupled to the master grip to receive the alignment of the master grip and (ii) coupled to the slave surgical instrument, to control motion of the slave by continuously reducing the alignment error, as the master grip moves, without autonomous motion of the slave surgical instrument tip and without autonomous motion of the master grip.

The ratcheting system further includes an introduce control system error controller for introducing a control system error with respect to the alignments of the slave surgical instrument tip and the master grip.

The introduce control system error controller includes, but is not limited to, any one of or any combination of:
  1. Penalizing slave angular velocity based on the amount of rotation angle error;
  2. Imposing artificial joint limits on the motion of slave surgical instrument tip based on a rotation angle error.
  3. Low-pass filtering the sensed master grip rotation; and
  4. Low-pass filtering the commanded slave surgical instrument tip rotation.

In another aspect, the ratcheting system includes a multiple orientation solution controller for determining an orientation solution closest to an orientation of the master grip. The multiple orientation controller can be included in any combination of controllers, including but not limited to the introduce control system error controller. In one aspect, the multiple orientation solution controller includes an upside down controller.

In another aspect, a method for controlling alignment of a slave surgical instrument tip in a minimally invasive surgical system with alignment of a master grip in the minimally invasive surgical system comprises:
  receiving, by a ratcheting system in the minimally invasive surgical system, an alignment of the slave surgical instrument tip in a common frame of reference and an alignment of the master grip in the common frame of reference; and
  ratcheting, by the ratcheting system, the alignment of the slave surgical instrument tip to the alignment of the master grip by continuously reducing an alignment error in the common frame of reference between the alignments, as the master grip moves, without autonomous motion of the slave surgical instrument tip and without autonomous motion of the master grip.

In one aspect, the ratcheting further comprises:
  introducing a control system error between the slave surgical instrument tip alignment and the master grip alignment.

The introducing a control system error includes, but is not limited to, any one of or any combination of:
  1. Penalizing slave angular velocity based on the amount of rotation angle error;
  2. Imposing artificial joint limits on the motion of slave surgical instrument tip based on a rotation angle error.
  3. Low-pass filtering the sensed master grip rotation; and
  4. Low-pass filtering the commanded slave surgical instrument tip rotation.

In still another aspect, the ratcheting further comprises selecting an orientation solution from a group of orientation solutions based on an orientation, in the common frame of reference, of the master grip. In one aspect, the selecting an orientation solution is in combination with the introducing a control system error. In another aspect, the selecting an orientation solution includes selecting an upside down solution.

What is claimed is:
1. A teleoperated system comprising:
  a robotic means configured to support an instrument;
  an input means configured to be manipulated by an operator to command motion of the instrument; and a ratcheting means configured to:
  determine first rotation values describing an orientation of the input means,
  determine second rotation values describing an orientation of the instrument,
  determine, based on the first rotation values and the second rotation values, an orientation error between the orientation of the input means and the orientation of the instrument,
  generate, based on the orientation error, a motion command for the instrument to reduce the orientation error by increasing an alignment between the input means and the instrument, and
  command the robotic means to move in accordance with the motion command.

2. The teleoperated system of claim 1, wherein to generate the motion command, the ratcheting means is configured to:
  selectively impose, based on the orientation error, an artificial joint limit on a commanded movement of the instrument.

3. The teleoperated system of claim 2, wherein the ratcheting means is further configured to:
  determine, based on the orientation error, the artificial joint limit, wherein the artificial joint limit widens as the orientation error decreases.

4. The teleoperated system of claim 2, wherein the artificial joint limit allows the instrument to move in a same relative direction as the input means until the artificial joint limit is reached.

5. The teleoperated system of claim 2, wherein the ratcheting means is further configured to:
  apply force feedback to the input means when the artificial joint limit has been reached.

6. The teleoperated system of claim 1, wherein to generate the motion command, the ratcheting means is configured to:
  low-pass filter the first rotation values or the second rotation values, wherein a cutoff frequency for the low-pass filtering is determined based on the orientation error, and
  generate, based on the low-pass filtered first rotation values or the low-pass filtered second rotation values, the motion command.

7. The teleoperated system of claim 6, wherein the ratcheting means determines the cutoff frequency according to a monotonic penalty profile and the orientation error.

8. The teleoperated system of claim 1, wherein to generate the motion command, the ratcheting means is configured to:
  determine, based on the orientation error, a velocity penalty, and
  penalize, based on the velocity penalty, an angular velocity of the motion command.

9. The teleoperated system of claim 8, wherein to determine the velocity penalty, the ratcheting means is configured to:
  apply a continuous and monotonic penalty profile.

10. The teleoperated system of claim 8, wherein to determine the velocity penalty, the ratcheting means is configured to:
  select, based on the orientation error, a scale factor, and
  scale, based on the scale factor, the angular velocity of the motion command.

11. The teleoperated system of claim 1, wherein the ratcheting means is further configured to use the orientation error to generate the motion command only if the orientation error is smaller than a previous orientation error between the input means and the instrument.

12. The teleoperated system of claim 1, wherein the orientation of the instrument is an orientation of a tip of the instrument.

13. The teleoperated system of claim 1, wherein the ratcheting means is further configured to:
  determine if the input means is right-side-up or upside-down; and
  determine the orientation error further based on whether the input means is right-side-up or upside-down.

14. The teleoperated system of claim 13, wherein when the input means is upside-down, the ratcheting means is further configured to rotate a relative rotation matrix characterizing the orientation error before determining the orientation error.

15. A method of controlling a teleoperated system comprising a robotic means configured to support an instrument, the method comprising:
  determining, by a ratcheting means of the teleoperated system, first rotation values describing an orientation of an input means configured to be manipulated by an operator to command motion of the instrument;
  determining, by the ratcheting means, second rotation values describing an orientation of the instrument;
  determining, by the ratcheting means based on the first rotation values and the second rotation values, an orientation error between the orientation of the input means and the orientation of the instrument;
  generating, by the ratcheting means and based on the orientation error, a motion command for the instrument to reduce the orientation error by increasing an alignment between the input means and the instrument; and
  commanding, by the ratcheting means, the robotic means to move in accordance with the motion command.

16. The method of claim 15, wherein generating the motion command comprises:
  selectively imposing, based on the orientation error, an artificial joint limit on a commanded movement of the instrument.

17. The method of claim 15, wherein generating the motion command comprises:
  low-pass filtering the first rotation values or the second rotation values, wherein a cutoff frequency for the low-pass filtering is determined based on the orientation error; and
  generating, based on the low-pass filtered first rotation values or the low-pass filtered second rotation values, the motion command.

18. The method of claim 15, wherein generating the motion command comprises:
  determining, based on the orientation error, a velocity penalty; and
  penalizing, based on the velocity penalty, an angular velocity of the motion command.

19. A non-transitory computer-readable medium comprising computer-readable code which, when executed by a ratcheting means associated with a teleoperated system comprising a robotic means configured to support an instrument, are adapted to cause the ratcheting means to perform a method comprising:
  determining first rotation values describing an orientation of an input means configured to be manipulated by an operator to command motion of the instrument;
  determining second rotation values describing an orientation of the instrument;

determining, based on the first rotation values and the second rotation values, an orientation error between the orientation of the input means and the orientation of the instrument;

generating, based on the orientation error, a motion command for the instrument to reduce the orientation error by increasing an alignment between the input means and the instrument; and commanding the robotic means to move in accordance with the motion command.

20. The non-transitory computer-readable medium of claim 19, wherein generating the motion command comprises:

selectively imposing, based on the orientation error, an artificial joint limit on a commanded movement of the instrument; or low-pass filtering the first rotation values or the second rotation values, wherein a cutoff frequency for the low-pass filtering is determined based on the orientation error, and generating, based on the low-pass filtered first rotation values or the low-pass filtered second rotation values, the motion command; or determining, based on the orientation error, a velocity penalty, and penalizing, based on the velocity penalty, an angular velocity of the motion command.

\* \* \* \* \*